(12) United States Patent
Stickney et al.

(10) Patent No.: US 8,663,121 B2
(45) Date of Patent: Mar. 4, 2014

(54) PULSE DETECTION METHOD AND APPARATUS USING PATIENT IMPEDANCE

(75) Inventors: Ronald E. Stickney, Edmonds, WA (US); James W. Taylor, Sammamish, WA (US); Patricia O'Hearn, Mercer Island, WA (US); Cynthia P. Jayne, Redmond, WA (US); Paula Lank, Renton, WA (US); David R. Hampton, Woodville, WA (US)

(73) Assignee: Physio-Control, Inc., Redmond, WA (US)

( * ) Notice: Subject to any disclaimer, the term of this patent is extended or adjusted under 35 U.S.C. 154(b) by 427 days.

(21) Appl. No.: 12/688,684

(22) Filed: Jan. 15, 2010

(65) Prior Publication Data

US 2010/0121208 A1    May 13, 2010

Related U.S. Application Data

(62) Division of application No. 11/737,703, filed on Apr. 19, 2007, now Pat. No. 8,092,392, which is a division of application No. 10/013,941, filed on Dec. 6, 2001, now abandoned.

(51) Int. Cl.
*A61B 5/0452* (2006.01)

(52) U.S. Cl.
USPC ........................................... 600/508

(58) Field of Classification Search
USPC ............... 600/373, 377, 500, 508, 547; 607/5
See application file for complete search history.

(56) References Cited

U.S. PATENT DOCUMENTS

| | | | |
|---|---|---|---|
| 3,452,743 A * | 7/1969 | Rieke | 600/547 |
| 3,716,059 A | 2/1973 | Welborn et al. | |
| 3,871,359 A | 3/1975 | Pacela | |
| RE30,101 E | 9/1979 | Kubicek et al. | |
| 4,181,134 A | 1/1980 | Mason et al. | |
| 4,220,160 A | 9/1980 | Kimball et al. | |
| RE30,750 E | 9/1981 | Diack et al. | |

(Continued)

FOREIGN PATENT DOCUMENTS

| EP | 0339471 A2 | 11/1989 |
|---|---|---|
| EP | 0435500 A1 | 7/1991 |

(Continued)

OTHER PUBLICATIONS

Office action from U.S. Appl. No. 11/187,616, dated Dec. 23, 2010, 6 pages.

(Continued)

*Primary Examiner* — Christopher D Koharski
*Assistant Examiner* — Frances Oropeza
(74) *Attorney, Agent, or Firm* — Marger Johnson & McCollom PC

(57) ABSTRACT

The presence of a cardiac pulse in a patient is determined by evaluating fluctuations in an electrical signal that represents a measurement of the patient's transthoracic impedance. Impedance signal data obtained from the patient is analyzed for a feature indicative of the presence of a cardiac pulse. Whether a cardiac pulse is present in the patient is determined based on the feature in the impedance signal data. Electrocardiogram (ECG) data may also be obtained in time coordination with the impedance signal data. Various applications for the pulse detection of the invention include detection of PEA and prompting PEA-specific therapy, prompting defibrillation therapy and/or CPR, and prompting rescue breathing depending on detection of respiration.

16 Claims, 10 Drawing Sheets

(56) References Cited

U.S. PATENT DOCUMENTS

| | | | |
|---|---|---|---|
| 4,291,699 A | 9/1981 | Geddes et al. | |
| 4,428,380 A | 1/1984 | Wong et al. | |
| 4,446,873 A | 5/1984 | Groch et al. | |
| 4,450,527 A | 5/1984 | Sramek | |
| 4,519,397 A | 5/1985 | Tabata | |
| 4,548,204 A | 10/1985 | Groch et al. | |
| 4,559,946 A | 12/1985 | Mower | |
| 4,562,843 A | 1/1986 | Djordjevich et al. | |
| 4,610,254 A | 9/1986 | Morgan et al. | |
| 4,777,962 A | 10/1988 | Watson et al. | |
| 4,792,145 A | 12/1988 | Eisenberg et al. | |
| 4,896,675 A | 1/1990 | Ohsuga et al. | |
| 4,919,145 A | 4/1990 | Marriott | |
| 4,928,690 A | 5/1990 | Heilman et al. | |
| 4,947,859 A | 8/1990 | Brewer et al. | |
| 4,951,679 A | 8/1990 | Harada | |
| 4,955,381 A | 9/1990 | Way et al. | |
| 4,967,760 A | 11/1990 | Bennett, Jr. et al. | |
| 5,002,052 A | 3/1991 | Haluska | |
| 5,035,247 A | 7/1991 | Heimann | |
| 5,036,857 A | 8/1991 | Semmlow et al. | |
| 5,077,667 A | 12/1991 | Brown et al. | |
| 5,078,134 A | 1/1992 | Heilman et al. | |
| 5,178,154 A | 1/1993 | Ackmann et al. | |
| 5,184,620 A | 2/1993 | Cudahy et al. | |
| 5,243,975 A | 9/1993 | Alferness et al. | |
| 5,261,418 A | 11/1993 | Ferek-Petric | |
| 5,273,036 A | 12/1993 | Kronberg et al. | |
| 5,305,745 A | 4/1994 | Zacouto | |
| 5,318,592 A | 6/1994 | Schaldach | |
| 5,330,506 A | 7/1994 | Alferness et al. | |
| 5,337,752 A | 8/1994 | Reeves | |
| 5,339,819 A | 8/1994 | Takashima | |
| 5,353,793 A | 10/1994 | Bornn | |
| 5,362,966 A | 11/1994 | Rosenthal et al. | |
| 5,366,486 A | 11/1994 | Zipes et al. | |
| 5,392,780 A | 2/1995 | Ogino et al. | |
| 5,404,877 A | 4/1995 | Nolan et al. | |
| 5,405,362 A | 4/1995 | Kramer et al. | |
| 5,423,326 A | 6/1995 | Wang et al. | |
| 5,425,750 A | 6/1995 | Moberg | |
| 5,431,688 A | 7/1995 | Freeman | |
| 5,433,731 A | 7/1995 | Hoegnelid et al. | |
| 5,443,072 A | 8/1995 | Kagan et al. | |
| 5,458,621 A | 10/1995 | White et al. | |
| RE35,122 E | 12/1995 | Corenman et al. | |
| 5,474,574 A | 12/1995 | Payne et al. | |
| 5,490,516 A | 2/1996 | Hutson | |
| 5,497,779 A | 3/1996 | Takaya et al. | |
| 5,617,868 A | 4/1997 | Harada et al. | |
| 5,620,003 A | 4/1997 | Sepponen | |
| 5,622,182 A | 4/1997 | Jaffe | |
| 5,683,424 A | 11/1997 | Brown et al. | |
| 5,685,317 A | 11/1997 | Sjostrom | |
| 5,687,738 A | 11/1997 | Shapiro et al. | |
| 5,700,283 A | 12/1997 | Salo | |
| 5,702,427 A | 12/1997 | Ecker et al. | |
| 5,704,363 A | 1/1998 | Amano | |
| 5,713,933 A * | 2/1998 | Condie et al. | 607/28 |
| 5,727,561 A | 3/1998 | Owsley | |
| 5,776,071 A | 7/1998 | Inukai et al. | |
| 5,795,300 A | 8/1998 | Bryars | |
| 5,807,268 A | 9/1998 | Reeves et al. | |
| 5,825,895 A | 10/1998 | Grasfield et al. | |
| 5,885,222 A | 3/1999 | Kassal et al. | |
| 6,005,658 A | 12/1999 | Kaluza et al. | |
| 6,050,950 A | 4/2000 | Mohler | |
| 6,053,872 A | 4/2000 | Mohler | |
| 6,104,953 A | 8/2000 | Leyde | |
| 6,122,536 A | 9/2000 | Sun et al. | |
| 6,125,298 A | 9/2000 | Olson et al. | |
| 6,125,299 A | 9/2000 | Groenke et al. | |
| 6,141,584 A | 10/2000 | Rockwell et al. | |
| 6,155,257 A | 12/2000 | Lurie et al. | |
| 6,161,038 A | 12/2000 | Schookin et al. | |
| 6,171,256 B1 | 1/2001 | Joo et al. | |
| 6,179,783 B1 | 1/2001 | Mohler | |
| 6,293,915 B1 | 9/2001 | Amano et al. | |
| 6,298,267 B1 | 10/2001 | Rosborough et al. | |
| 6,304,773 B1 | 10/2001 | Taylor et al. | |
| 6,304,780 B1 | 10/2001 | Owen et al. | |
| 6,312,399 B1 | 11/2001 | Lurie et al. | |
| 6,341,233 B1 * | 1/2002 | Hastings et al. | 607/9 |
| 6,356,785 B1 | 3/2002 | Snyder et al. | |
| 6,371,920 B1 | 4/2002 | Kamimoto et al. | |
| 6,415,175 B1 * | 7/2002 | Conley et al. | 600/523 |
| 6,428,483 B1 | 8/2002 | Carlebach | |
| 6,440,082 B1 | 8/2002 | Joo et al. | |
| 6,443,906 B1 | 9/2002 | Ting et al. | |
| 6,501,983 B1 | 12/2002 | Natarajan et al. | |
| 6,575,914 B2 | 6/2003 | Rock et al. | |
| 6,587,723 B1 | 7/2003 | Sloman et al. | |
| 6,650,940 B1 | 11/2003 | Zhu et al. | |
| 2001/0008953 A1 * | 7/2001 | Honda et al. | 600/301 |
| 2001/0039383 A1 | 11/2001 | Mohler | |
| 2001/0047140 A1 | 11/2001 | Freeman | |
| 2002/0032383 A1 | 3/2002 | Weil et al. | |
| 2002/0072685 A1 | 6/2002 | Rymut et al. | |
| 2002/0165585 A1 | 11/2002 | Dupelle et al. | |
| 2002/0173725 A1 | 11/2002 | Rock et al. | |
| 2003/0060723 A1 | 3/2003 | Joo et al. | |
| 2003/0109790 A1 | 6/2003 | Stickney et al. | |
| 2004/0039419 A1 | 2/2004 | Stickney et al. | |
| 2004/0039420 A1 | 2/2004 | Jayne et al. | |
| 2005/0240234 A1 | 10/2005 | Joo et al. | |
| 2009/0131997 A1 * | 5/2009 | Cohen et al. | 607/4 |
| 2010/0114219 A1 | 5/2010 | Stickney et al. | |
| 2010/0121208 A1 | 5/2010 | Stickney et al. | |
| 2010/0121392 A1 | 5/2010 | Stickney et al. | |

FOREIGN PATENT DOCUMENTS

| | | |
|---|---|---|
| EP | 1057498 A2 | 12/2000 |
| GB | 2150332 | 6/1985 |
| WO | 8401705 | 5/1984 |
| WO | 9322970 A1 | 11/1993 |
| WO | 9705821 A1 | 2/1997 |
| WO | 0122885 A1 | 4/2001 |

OTHER PUBLICATIONS

Office Action from U.S. Appl. No. 11/187,616, dated Jul. 29, 2011, 7 pages.

Pre-Appeal Brief Request for Review for U.S. Appl. No. 11/187,616, dated Sep. 19, 2011, 5 pages.

Office Action from U.S. Appl. No. 13/032,250, dated Oct. 6, 2011, 11 pages.

Response to Office Action dated Oct. 6, 2011, from U.S. Appl. No. 13/032,250, filed Dec. 6, 2011, 12 pages.

Iwata et al., "Pattern Classification of the Phonocardiogram Using Linear Prediction Analysis, " Medical & Biological Engineering & Computing 15(4):407-412, Jul. 1977.

"American Heart Guidelines 2000 for Cardiopulmonary Resuscitation and Emergency Cardiovasular Care, Part 3: Adult Basic Life Support," Circulation 102 Suppl. I:1-22 to 1-59, 2000.

Bulgrin, J.R., et al., "Comparison of Short-time Fourier, Wavelet and Time-domain Analyses of Intracardiac Sounds" Biomedical Sciences Instrumentation 29:465-472, 1993, ISA Paper #93-059.

Kassal, J., et al., "Polymer-Based Adherent Differential-Output Sensor for Cardiac Auscultation," Medical Electronics, Sep. 1994, pp. 54-63.

L. Cobb et al., "Influence of Cardiopulmonary Resuscitation Prior to Defibrillation in Patients With Out-of-Hospital Ventricular Fibrillation," JAMA 281:1182-1188 (1999).

"±5 g to ±50 g, Low Noise, Low Power, Single/Dual Axis iMEMS® Accelerometers (ADXL150/ADXL250-Specifications)," Analog Devices, Inc., Rev. 0,1998, 8 pp.

R. Duda and P. Hart, "Pattern Classification and Scene Analysis," published by John Wiley & Sons, New York, pp. 1-482, (1973).

Gravenstein, J.S., et al., $CO_2$: Gas Monitoring in Clinical Practice, 2d ed., Butterworth-Heinemann, Boston, 1995, Chap. 4, "Monitoring Carbon Dioxide," pp. 23-42.

(56) References Cited

OTHER PUBLICATIONS

Gulcur et al., "Estimation of Systolic Blood Pressure from the Second Heart Sounds," 2nd International Biomedical Engineering Days, 1998, pp. 39-40.
Hasegawa, M.D., and S. Rodbard, M.D., Ph.D., "Delayed Timing of Heart and Arterial Sounds in Patients with Implanted Pacemakers," Journal of Thoracic and Cardiovascular Surgery 72(1):62-66, Jul. 1976.
S.M. Kay, "Modem Spectral Estimation: Theory and Application," published by Prentice Hall of Englewood Cliffs, New Jersey pp. 182-183 (1988).
Lehner, R.J.; Rangayyan, R.M., "Microcomputer System for Quantification of the Phonocardiogram," Proceedings of the Seventh Annual Conference of the IEEE/Engineering in Medicine and Biology Society 2(2):849-854, 1986.
Luisada, A.A., "The First Heart Sound in Normal and Pathological Conditions," Japanese Heart Journal, 28(2):143-156, Mar. 1987.
Measurement Specialities, Inc., "Piezo Film Sensors Technical Manual," Internet Version, Aug. 1998, 89 pp.
Stodieck, L.S., and M.W. Luttges, "Relationships Between the Electrocardiogram and Phonocardiogram: Potential for Improved Heart Monitoring," ISA Transactions, 23(4):59-65, Apr. 1984.
Office Action from U.S. Appl. No. 11/167,247, dated Oct. 1, 2008, 12 pp.
Response to Office Action dated Oct. 1, 2008, from U.S. Appl. No. 11/167,247, filed Feb. 2, 2009, 16 pp.
Office Action from U.S. Appl. No. 11/167,247, dated Apr. 30, 2009, 6 pp.
Response to Office Action dated Apr. 30, 2009, from U.S. Appl. No. 11/167,247, filed Jul. 30, 2009, 19 pp.
Advisory Action from U.S. Appl. No. 11/167,247, dated Aug. 14, 2009, 3, pp.
Response to Advisory Action dated Aug. 14, 2009, from U.S. Appl. No. 11/167,247, filed filed Sep. 30, 2009, 20 pp.
Office Action from U.S. Appl. No. 11/167,247, dated Dec. 29, 2009, 5 pp.
Response to Office Action dated Dec. 29, 2009, from U.S. Appl. No. 11/167,247, filed Mar. 26, 2010, 15 pp.
Office Action from U.S. Appl. No. 11/167,247, dated Jun. 28, 2010, 5 pp.
Restriction Requirement from U.S. Appl. No. 11/187,616, dated Dec. 4, 2008, 9 pp.
Response to Restriction Requirement dated Dec. 4, 2008, from U.S. Appl. No. 11/187,616, filed Jan. 5, 2009, 2 pp.
Office Action from U.S. Appl. No. 11/187,616, dated Apr. 16, 2009, 11 pp.
Response to Office Action dated Apr. 16, 2009, from U.S. Appl. No. 11/187,616, filed Aug. 11, 2009, 31 pp.
Restriction Requirement from U.S. Appl. No. 11/187,616, dated Dec. 1, 2009, 9 pp.
Response to Restriction Requirement dated Dec. 1, 2009, from U.S. Appl. No. 11/187,616, filed Dec. 30, 2009, 2 pp.
Office Action from U.S. Appl. No. 11/187,616, dated Mar. 31, 2010, 9 pp.
Response to Office Action dated Mar. 31, 2010, from U.S. Appl. No. 11/187,616, filed May 28, 2010, 7 pp.
Office Action from U.S. Appl. No. 11/187,616, dated Jul. 13, 2010, 7 pp.
Restriction Requirement from UU.S. Appl. No. 10/229,339, dated Sep. 6, 2005, 6 pp.
Response to Restriction Requirement dated Sep. 6, 2005, from U.S. Appl. No. 10/229,339, dated Oct. 6, 2005, 5 pp.
Office Action from U.S. Appl. No. 10/229,339, dated Dec. 27, 2005, 12 pp.
Response to Office Action dated Dec. 27, 2005, from U.S. Appl. No. 10/229,339, filed Jun. 5, 2006, 30 pp.
Office Action from U.S. Appl. No. 10/229,339, dated Oct. 12, 2006, 9 pp.
Restriction Requirement from U.S. Appl. No. 11/737,703, dated Dec. 2, 2009, 6 pp.
Response to Restriction Requirement dated Dec. 2, 2009, from U.S. Appl. No. 11/737,703, dated Dec. 30, 2009, 5 pp.
Office Action from U.S. Appl. No. 11/737,703, dated Apr. 15, 2010, 7 pp.
Response to Office Action dated Apr. 15, 2010, from U.S. Appl. No. 11/737,703, filed Jul. 14, 2010, 6 pp.
Geddes et al., "Cyclops Whistler—A Noninvasive Audible Monitor for the Amplitude of the Arterial Pulse," Cardiovascular Engineering, vol. 5, No. 2, 97-102, 2005.
Farag et al., "Detection of pulse and respiratory signals from the wrist using dry electrodes," Biomedical instrumentation technology Association for the Advancement of Medical Instrumentation, Jul./Aug. 1994, 5 pp.
Renevey et al., "Wrist-located pulse detection using IR signals, activity and nonlinear artifact cancellation," 2001 Conference Proceedings of the 23rd Annual International Conference of the IEEE Engineering in Medicine and Biology Society, Istanbul, Turkey, Oct. 25-28, 2001, 4 pp.
Tibballs et al., "Reliability of pulse palpation by health care personnel to diagnose pediatric cardiac arrest," Resuscitation, 2009;80:61-64.
Lapostolle et al., "Basic cardiac life support providers checking the carotid pulse: performance, degree of conviction, and influencing factors," Acad Emerg Med. 2004; 11:878-880.
Kubicek et al., Development and Evaluation of an Impedance Cardiographic System to Measure Cardiac Output and Other Cardiac Parameters, National Aeronautics and Space Administration (NASA), Jul. 1, 1968 to Jun. 30, 1969, 472 pp.
Kubicek et al., "Impedance Cardiography as a Noninvasive Method of Monitoring Cardiac Function and Other Parameters of the Cardiovascular System," Annals of the New York Academy of Sciences 170, No. 2 (Jul. 1, 1970): 724-732.
Responsive Amendment to Office Action dated Dec. 23, 2010, from U.S. Appl. No. 11/187,616, filed May 20, 2011, 9 pp.
Office Action from U.S. Appl. No. 11/737,703, dated Nov. 1, 2010, 7 pp.
Response to Office Action dated Nov. 1, 2010, from U.S. Appl. No. 11/737,703, filed Jan. 31, 2011, 6 pp.
Alt et al., "Feasibility of Using Intracardiac Impedance Measurements for Capture Detection," Pacing and Clinical Electrophysiology 15: 1873-1879, Nov., Part II, 1992.
Bahr at al., "Skills of Lay People in Checking the Carotid Pulse," Resuscitation 35:23-26, 1997.
Bogaard et al., "Assessment of the Haemodynamic Response to Exercise by Means of Electrical Impedance Cardiography: Method, Validation and Clinical Applications," Physiological Measurement 18:95-105, May 1997.
CardioDynamics, What Is the BioZ@ ICG Test?http://www.cardiodynamics.com/cdpatil0.html, accessed Jun. 3, 2002.
Eberle et al., "Checking the Carotid Pulse Check: Diagnostic Accuracy of First Responders in Patients With and Without a Pulse," Resuscitation 33: 107-116, 1996.
Hoffman et al., "Respiratory Monitoring With a New Impedance Plethysmograph," Anaesthesia 41: 1139-1142, 1986.
Hu et al., "A Study on Methods for Impedance Cardiography," Proceedings-19th International Conference-IEEE/EMBS, Chicago, Oct. 30-Nov. 2,1997, pp. 2074-2077.
Johnston et al., "The Transthoracic Impedance Cardiogram is a Potential Haemodynamic Sensor for an Automated External Defibrillator," European Heart Journal 19: 1879-1888, Dec. 1998.
Kubicek, et al, "Development and Evaluation of an Impedance Cardiac Output System," Aerospace Medicine 37: 1208-12 Dec. 12, 1966.
Mehlsen et al., "A Comparison of Systolic Time Intervals Measured by Impedance Cardiography and Carotid Pulse Tracing," Danish Medical Bulletin 37(1):93-95, Feb. 1990.
Muzi et al., "Clinical Application of ECG R-Wave Triggered, Ensemble-Averaged Impedance Waveforms," Annual International Conference of the IEEE Engineering in Medicine and Biology Society 12(5): 1091, 1990.
Rosell et al., "Signal-to-Motion Artifact Ratio Versus Frequency for Impedance Pneumography," IEEE Transactions on Biomedical Engineering 42(3): 321-323, Mar. 1995.

(56) References Cited

OTHER PUBLICATIONS

Wang et al., "Impedance Cardiac Profile Monitoring by a Modified Ensemble Averaging Technique," Proceedings of the IEEE Engineering in Medicine and Biology Society 10th Annual International Conference 1:39-40, New Orleans, 1988.

Watanabe et al., "Computer Analysis of the Exercise ECG: A Review," Progress in Cardiovascular Diseases XX11 (6):423-446, May-Jun. 1980.

Woltjer et al., "The Technique of Impedance Cardiography," European Heart Journal 18: 1396-1403, Sep. 1997.

Geddes et al., Principals of Applied Biomedical Instrumentation, Third edition, John Wiley and Sons, New York., 1989, "Applications of Ultrasound," pp. 184-209.

Ochoa et al., "Competence of Health Professionals to Check the Carotid Pulse," Resuscitation 37: 173-175, 1998.

CardioDynamics, BioZ Technology, "ICG Technology," http://www.cardiodynamics.com/cdprod40.html, accessed Jun. 2002.

Office Action from U.S. Appl. No. 10/013,941, dated Jun. 3, 2003, 5 pp.

Response to Office Action dated Jun. 3, 2003, from U.S. Appl. No. 10/013,941, filed Jun. 27, 2003, 2 pp.

Office Action from U.S. Appl. No. 10/013,941, dated Aug. 22, 2003, 7 pp.

Response to Office Action dated Aug. 22, 2003, from U.S. Appl. No. 10/013,941, filed Jan. 8, 2004, 11 pp.

Office Action from U.S. Appl. No. 10/013,941, dated Mar. 31, 2004, 11 pp.

Response to Office Action dated Mar. 31, 2004, from U.S. Appl. No. 10/013,941, filed Apr. 13, 2004, 3 pp.

Office Action from U.S. Appl. No. 10/013,941, dated May 5, 2004, 10 pp.

Response to Office Action dated May 5, 2004, from U.S. Appl. No. 10/013,941, filed May 25, 2004, 6 pp.

Advisory Action from U.S. Appl. No. 10/013,941, dated Jul. 26, 2004, 3 pp.

Office Action from U.S. Appl. No. 101013,941, dated Jan. 7, 2005, 7 pp.

Response to Office Action dated Jan. 7, 2005, from U.S. Appl. No. 10/013,941, filed May 10, 2005, 11 pp.

Office Action from U.S. Appl. No. 10/013,941, dated Jul. 25, 2005, 7 pp.

Office Action from U.S. Appl. No. 10/013,941, dated Mar. 22, 2006, 11 pp.

Response to Office Action dated Mar. 22, 2006, from U.S. Appl. No. 10/013,941, filed Oct. 3, 2006, 6 pp.

Office Action from U.S. Appl. No. 10/013,941, dated Dec. 19, 2006, 9 pp.

International Preliminary Report on Patentability from international application No. PCT/US02/39240, dated Feb. 17, 2004, 3 pp.

* cited by examiner

PULSE DETECTION METHOD AND APPARATUS USING PATIENT IMPEDANCE

RELATED APPLICATION

This application is a divisional of U.S. patent application Ser. No. 11/737,703, filed Apr. 19, 2007, which is a divisional of U.S. patent application Ser. No. 10/013,941, filed on Dec. 6, 2001, and now abandoned. The entire content of each of these applications is incorporated herein by reference.

FIELD OF THE INVENTION

The invention relates generally to the detection of cardiac activity in a patient, and more specifically, to a method and apparatus for cardiac pulse detection.

BACKGROUND OF THE INVENTION

The presence of cardiac pulse in a patient is presently detected preferably by palpating the patient's neck and sensing changes in the volume of the patient's carotid artery due to blood pumped from the patient's heart. If a pulse can be felt at the carotid artery, it is likely that the patient's heart is pumping sufficient blood to support life. A graph representative of the physical expansion and contraction of a patient's carotid artery during two consecutive pulses, or heartbeats, is shown at the top of FIG. 1. When the heart's ventricles contract during a heartbeat, a pressure wave is sent throughout the patient's peripheral circulation system. The carotid pulse shown in FIG. 1 rises with the ventricular ejection of blood at systole and peaks when the pressure wave from the heart reaches a maximum. The carotid pulse falls off again as the pressure subsides toward the end of each pulse.

An electrocardiogram (ECG) waveform describes the electrical activity of a patient's heart. The middle graph of FIG. 1 illustrates an example of an ECG waveform for two heartbeats corresponding in time with the carotid pulse. Referring to the first shown heartbeat, the portion of the ECG waveform representing depolarization of the atrial muscle fibers is referred to as the "P" wave. Depolarization of the ventricular muscle fibers is collectively represented by the "Q," "R," and "S" waves of the ECG waveform. Finally, the portion of the waveform representing repolarization of the ventricular muscle fibers is known as the "T" wave. Between heartbeats, the ECG waveform returns to an isopotential level.

Discussed herein with respect to the present invention is the correlation of fluctuations in a patient's transthoracic impedance with blood flow that occurs with each cardiac pulse wave. The bottom graph of FIG. 1 illustrates an example of a filtered impedance signal for a patient in which fluctuations in impedance correspond in time with the carotid pulse and ECG waveform.

The lack of a detectable cardiac pulse in a patient is a strong indicator of cardiac arrest. Cardiac arrest is a life-threatening medical condition in which the patient's heart fails to provide enough blood flow to support life. During cardiac arrest, the electrical activity may be disorganized (ventricular fibrillation), too rapid (ventricular tachycardia), absent (asystole), or organized at a normal or slow heart rate (pulseless electrical activity). A caregiver may apply a defibrillation shock to a patient in ventricular fibrillation (VF) or ventricular tachycardia (VT) to stop the unsynchronized or rapid electrical activity and allow a perfusing rhythm to commence. External defibrillation, in particular, is provided by applying a strong electric pulse to the patient's heart through electrodes placed on the surface of the patient's body. If a patient lacks a detectable pulse but has an ECG rhythm of asystole or pulseless electrical activity (PEA), an appropriate therapy includes cardiopulmonary resuscitation (CPR), which causes some blood flow.

Before providing defibrillation therapy or CPR to a patient, a caregiver must first confirm that the patient is in cardiac arrest. In general, external defibrillation is suitable only for patients that are unconscious, apneic (i.e., not breathing), pulseless, and in VF or VT. Medical guidelines indicate that the presence or absence of a pulse in a patient should be determined within 10 seconds. See, "American Heart Guidelines 2000 for Cardiopulmonary Resuscitation and Emergency Cardiovascular Care, Part 3: Adult Basic Life Support," *Circulation* 102 suppl. I: I-22-I-59, 2000.

Unfortunately, under the pressures of an emergency situation, it can be extremely difficult for first-responding caregivers with little or no medical training to consistently and accurately detect a cardiac pulse in a patient (e.g., by palpating the carotid artery) in a short amount of time such as 10 seconds. See, Eberle B., et al., "Checking the Carotid Pulse Diagnostic Accuracy of First Responders in Patients With and Without a Pulse" *Resuscitation* 33: 107-116, 1996. Nevertheless, because time is of the essence in treating cardiac arrest, a caregiver may rush the preliminary evaluation, incorrectly conclude that the patient has no pulse, and proceed to provide defibrillation therapy when in fact the patient has a pulse. Alternatively, a caregiver may incorrectly conclude that the patient has a pulse and erroneously withhold defibrillation therapy. A need therefore exists for a method and apparatus that quickly, accurately, and automatically determines the presence of a pulse in a patient, particularly to prompt a caregiver to provide defibrillation or CPR therapy, as appropriate, in an emergency situation.

SUMMARY OF THE INVENTION

The present invention provides a method and apparatus that determines the presence of a cardiac pulse in a patient by evaluating fluctuations in an electrical signal that represents a measurement of the patient's transthoracic impedance. By physiologically associating impedance fluctuations with the presence of a cardiac pulse, the presence or absence of a cardiac pulse in the patient is determined.

In accordance with one aspect of the present invention, impedance signal data obtained from a patient is analyzed for a feature indicative of the presence of a cardiac pulse. Whether a cardiac pulse is present in the patient is determined based on the feature in the impedance signal data.

The feature in the impedance signal data may be obtained from evaluating an amplitude of the impedance signal data, an energy in the impedance signal data, and/or a pattern match statistic resulting from comparing the impedance signal data with a previously-identified impedance signal pattern known to predict the presence of a cardiac pulse. Other determination and classification techniques known in the art may be used for the evaluation.

As to evaluating the amplitude of the impedance signal data, low and high peak amplitude values in the impedance signal data may be located and the peak-to-peak change in the amplitude from the low to the high peak amplitude value may be calculated. The peak-to-peak change in amplitude, constituting a feature indicative of the presence of a cardiac pulse, may be compared to a threshold to determine the presence of a pulse.

As to evaluating energy in the impedance signal data, an energy calculation may be performed using impedance signal data obtained from the patient. The calculated energy, constituting feature indicative of the presence of a cardiac pulse, is compared to a predetermined threshold to determine whether a cardiac pulse is present in the patient.

As to analyzing the impedance signal data using pattern matching, the impedance signal data may be compared to a previously-identified impedance signal pattern known to predict the presence of a cardiac pulse. The comparison produces a pattern match statistic, constituting the feature indicative of the presence of a cardiac pulse, which is compared to a predetermined threshold to determine whether a cardiac pulse is present in the patient.

The impedance signal data may be obtained from the patient using defibrillation electrodes placed on the patient or using separate impedance-sensing electrodes placed on the patient. If separate electrodes are used, the present invention includes prompting application of the defibrillation electrodes to the patient if a cardiac pulse is determined not present in the patient.

In accordance with another aspect of the present invention, electrocardiogram (ECG) data is obtained from the patient in time coordination with the impedance signal data. A QRS complex located in the ECG data is used to select a segment of the impedance signal data for further analysis. If a pulse is present in the patient, the pulse should be detectable following the located QRS complexes.

In accordance with yet another aspect of the present invention, pulseless electrical activity (PEA) may be detected when the patient is determined pulseless and the patient is not experiencing ventricular defibrillation (VF), ventricular tachycardia (VT), or asystole. In circumstances where PEA is found present, the present invention includes prompting delivery of PEA-specific therapy to the patient. The present invention may be employed in a variety of devices that provide monitoring and/or therapy. If, for example, the patient is determined pulseless and experiencing VT with a pulse rate greater than 100 beats per minute, the present invention may prompt delivery of a defibrillation pulse. If a cardiac pulse is later found in the patient after delivery of the defibrillation pulse, the present invention may report the return of spontaneous circulation in the patient.

The present invention is further useful in evaluating capture while delivering pacing stimuli to a patient. If a cardiac pulse is not detected immediately following a pacing pulse, the current level of the pacing pulse may be increased until capture by the pacing stimuli is achieved.

Other applications and advantages of the present invention are readily apparent. For example, the invention may be implemented in an automated external defibrillator (AED) that prompts the user to perform cardiopulmonary resuscitation (CPR) based on the absence of a pulse in a patient. The AED may also prompt the user to provide rescue breathing depending on detection of respiration. In regard to the latter, the impedance signal data and other relevant information, such as the patient's ECG, may be analyzed to detect the presence of respiration in the patient.

Embodiments of the invention intended for trained medical personnel may provide a display of the impedance signal data that is representative of the presence or absence of a pulse in a patient. In that regard, the impedance signal data may be shown as a way form, as shown in FIG. 1. The impedance signal data may also be displayed as a bar.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

A device constructed in accordance with the present invention uses measurements of a patient's transthoracic impedance to determine the presence of a cardiac pulse in the patient. As will be appreciated from the description herein, the device may be a stand alone unit or it may be incorporated into another monitoring or therapy-providing device. In one suitable application, the present invention is implemented in a defibrillator, such as the defibrillator 10 shown in FIG. 2. A patient 40 is connected to the defibrillator 10 via electrodes 12, 14 placed on the skin of the patient. The defibrillator 10 uses the electrodes 12, 14 to deliver defibrillation pulses to the patient 40. The defibrillator 10 also uses the electrodes 12, 14 to obtain ECG signals from the patient 40.

Figure 1:
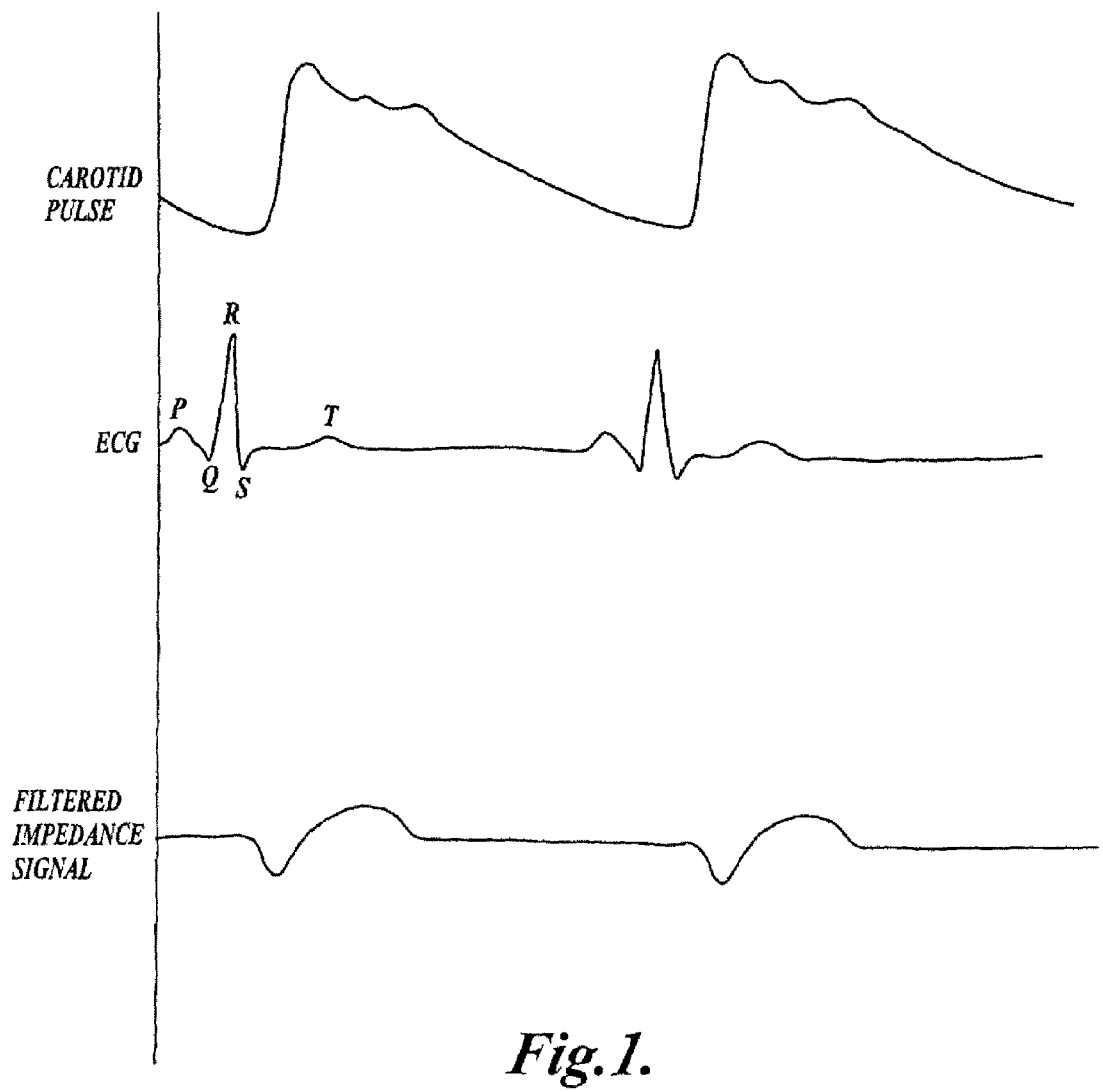
FIG. 1 is a pictorial diagram of a carotid pulse waveform, an electrocardiogram (ECG) waveform, and a filtered transthoracic impedance signal for two consecutive heartbeats reflecting fluctuations in transthoracic impedance that correspond with pulsatile blood flow.
Figure 2:
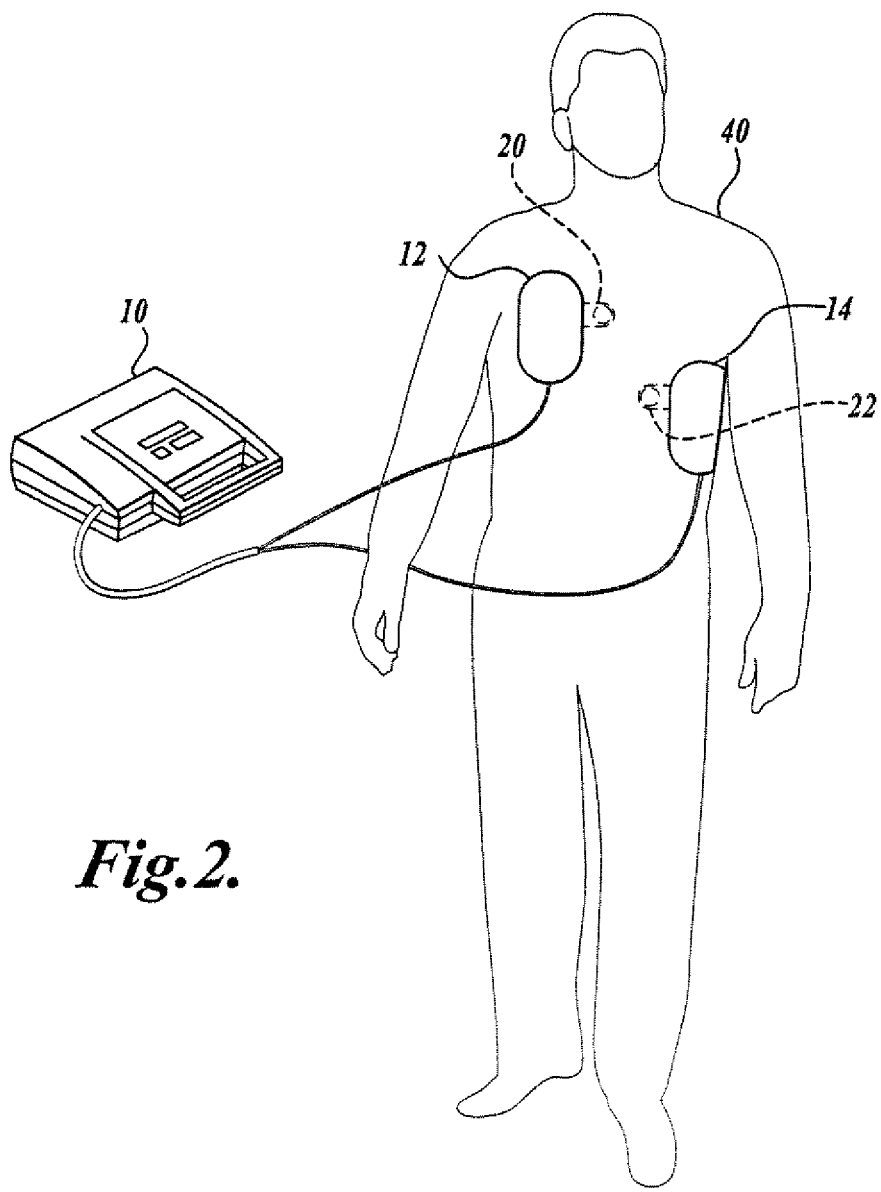
FIG. 2 is a pictorial diagram of a defibrillator and electrodes constructed in accordance with the present invention and attached to a patient.

The electrodes 12, 14 are further configured to communicate an impedance-sensing signal through the patient 40. The impedance-sensing signal is used by the defibrillator 10 to observe the patient's impedance. Alternatively, the defibrillator 10 may use sensors 20, 22 that are separate from the electrodes 12, 14 for communicating the impedance-sensing signal through the patient. The sensors 20, 22 may be connected to the electrodes 12, 14, as shown in FIG. 2, they may be attached to the patient 40 via separate wires (not shown) connected to the defibrillator 10. In either case, the sensors 20, 22 may be suitably constructed from standard external patient electrodes known in the art.

The defibrillator 10 measures the impedance of a patient between the electrodes 12, 14 (or between the sensors 20, 22, as the case may be) when placed on the patient 40. An impedance measuring component of the defibrillator 10 is preferably used to measure the patient's impedance.

A preferred embodiment of the invention uses a high-frequency, low-level constant current technique to measure the patient's transthoracic impedance, though other known impedance measuring techniques may be used. A signal generator included in the defibrillator 10 produces a low-amplitude, constant current, high-frequency signal (typically sinusoidal or square). The signal is preferably generated having a frequency in the range of 10 kHz-100 kHz. The current flows between the electrodes 12 and 14. The resulting current flow causes a voltage to develop across the patient's body that is proportional to the product of the patient's impedance and the applied current. To calculate the patient's impedance, the impedance measuring component in the defibrillator 10 divides the measured sensing voltage by the applied current. Since the measured voltage is linearly related to the patient's impedance, the impedance signal data used herein may either be a calculated impedance signal or the measured voltage signal.

While embodiments of the invention specifically described herein are shown implemented in a defibrillator 10, the present invention is not limited to such specific type of application. Those of ordinary skill in the art will recognize that the advantages of the invention may similarly be achieved by implementing the present invention in cardiac monitors and other types of medical equipment that do not necessarily provide defibrillation therapy.

Figure 3:
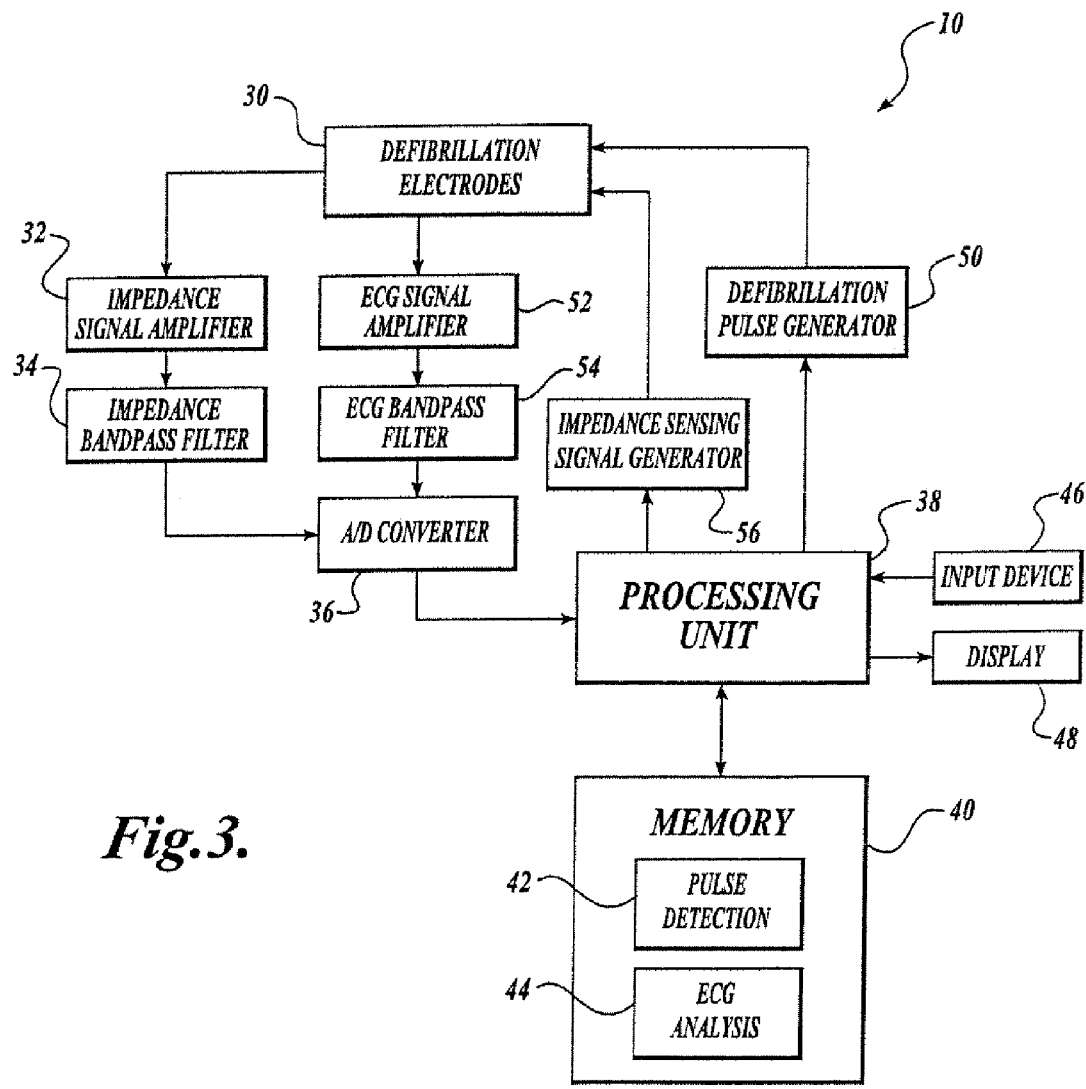
FIG. 3 is a block diagram of major components of the defibrillator shown in FIG. 2.

Prior to discussing various pulse detection processes that the defibrillator 10 may implement in accordance with the present invention, a brief description of certain major components of the defibrillator 10 is provided. Referring to FIG. 3, the defibrillator 10 includes defibrillation electrodes 30 (e.g., electrodes 12, 14 described above in FIG. 2). An impedance-sensing signal generator 56 communicates an impedance-sensing signal through the patient via the electrodes 30. A signal amplifier 32 amplifies the impedance-sensing signal to a level appropriate for digitization by analog-to-digital (A/D) converter 36. A bandpass filter 34 filters the amplified impedance-sensing signal to isolate the portion of the signal that most closely reveals fluctuations due to blood flow from cardiac pulses. In one embodiment of the invention, the bandpass filter 34 is a 1-10 Hz bandpass filter. Fluctuations in the impedance signal below 1 Hz are more likely to be caused by respiration in the patient, and not blood flow. Accordingly, the bandpass filter attenuates that component of the impedance signal. The portion of the impedance signal exceeding 10 Hz is more likely affected by surrounding noise and is likewise filtered out.

The filtered impedance signal is delivered to the A/D converter 36 that converts the impedance signal into digital impedance data for further evaluation. The bandpass filter 34 or other filter may be provided to reduce any aliasing introduced in the impedance signal by the A/D converter 36. The parameters of such filtering depend, in part, on the sampling rate of the A/D converter. Bandpass and antialiasing filters, as well as A/D converters, are well-known in the art, and may be implemented in hardware or software, or a combination of both. For example, a preferred embodiment uses a hardware lowpass filter on the impedance signal before the A/D converter 36, and then a software highpass filter on the digital impedance data after the A/D conversion. Another preferred embodiment additionally uses a software lowpass filter after the A/D conversion to further limit the bandwidth of the impedance signal. The A/D converter 36 delivers the digital impedance signal data to the processing unit 38 for evaluation.

The processing unit 38 evaluates the impedance signal data for the presence of a cardiac pulse. The processing unit 38 is preferably comprised of a computer processor that operates in accordance with programmed instructions stored in a memory 40 that implement a pulse detection process 42, described in more detail below. The processing unit 38 may also store in the memory 40 the impedance signal data obtained from the patient, along with other event data and ECG signal data. The memory 40 may be comprised of any type or combination of types of storage medium, including, for example, a volatile memory such as a dynamic random access memory (DRAM), a nonvolatile static memory, or storage media such as a magnetic tape or disk drive or optical storage unit (e.g., CD-RW).

The processing unit 38 may report the results of the pulse detection process to the operator of the defibrillator 10 via a display 48. The processing unit 38 may also prompt actions (e.g., CPR) to the operator to direct the resuscitation effort. The display 48 may include, for example, lights, audible signals, alarm, printer, or display screen. The display 48 may be in communication with the processing unit 38 and the processing unit 38 may be configured to prompt a message on the display 48, such as via the display screen, or an audible message, that reports whether a cardiac pulse is present in the patient. Further, the processing unit 38 may be configured to provide a graph on the display 48, such as via the display screen, that shows a representation of the impedance signal data. The processing unit 38 may also receive input from the operator of the defibrillator 10 via an input device 46. The input device 46 may include one or more keys, switches, buttons, or other types of user input devices.

The defibrillation electrodes 30 may further be used to sense the patient's electrocardiogram (ECG) signals. ECG signals obtained from the patient may be amplified and filtered in a conventional manner, and converted into digitized ECG data for evaluation by the processing unit 38. For example, the ECG signal may be amplified by an ECG signal amplifier 52 to an appropriate level, such as for digitization by the A/D converter 36. An ECG bandpass filter 54 filters the amplified ECG signal to isolate portions of the signal for further processing.

Preferably, the processing unit 38 evaluates the ECG signals in accordance with programmed instructions stored in the memory 40 that carry out an ECG evaluation process 44 to determine whether a defibrillation shock should be provided. A suitable method for determining whether to apply a defibrillation shock is described in U.S. Pat. No. 4,610,254, which is assigned to the assignee of the present invention and incorporated by reference herein. If the processing unit 38 determines that delivery of a defibrillation pulse is appropriate, the processing unit 38 instructs a defibrillation pulse generator 50 to prepare to deliver a defibrillation pulse to the patient. In that regard, the defibrillation pulse generator 50 uses an energy source (e.g., battery) to charge one or more defibrillation capacitors in the defibrillator 10.

When the defibrillation charge is ready for delivery, the processing unit 38 advises the operator via the display 48 that the defibrillator 10 is ready to deliver the defibrillation pulse. The processing unit 38 may ask the operator to initiate the delivery of the defibrillation pulse. When the operator initiates delivery of the defibrillation pulse (e.g., via the input device 46), the processing unit 38 instructs the defibrillation pulse generator 50 to discharge through the patient the energy stored in the defibrillation capacitors (via the electrodes 30).

Alternatively, the processing unit 38 may cause the defibrillation pulse generator 50 to automatically deliver the defibrillation pulse.

While FIG. 3 illustrates certain major components of the defibrillator 10, those having ordinary skill in the art will appreciate that the defibrillator 10 may contain more or fewer components than those shown. The disclosure of a preferred embodiment of the defibrillator 10 does not require that all of the general conventional components be shown. It will further be appreciated that the invention may be implemented in a cardiac monitor having essentially the same components as the defibrillator 10 shown in FIG. 3, except that the cardiac monitor does not have the components necessary for delivering a defibrillation pulse. Furthermore, some or all of the programmed instructions 42, 44 may be implemented in hardware as an alternative to software instructions stored in the memory 40.

As noted above, the present invention uses a portion of the impedance-sensing signal whose frequency range is most likely to reveal fluctuations indicating the presence of a cardiac pulse in the patient. The presence of characteristic fluctuations in patient impedance associated with a cardiac pulse is used to identify the presence of a cardiac pulse in the patient.

Figure 4:
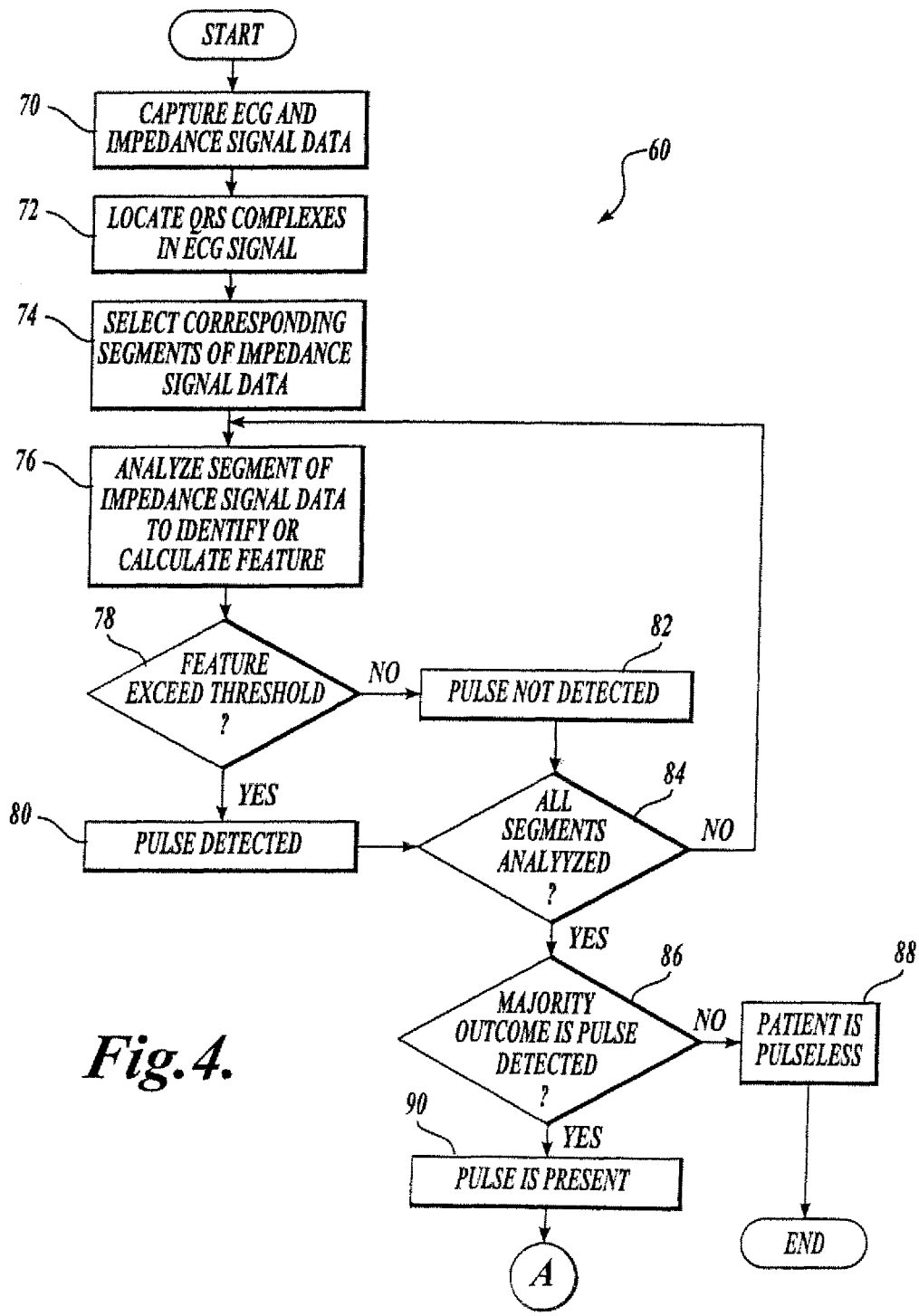
FIG. 4 is a flow diagram of a pulse detection process performed in accordance with the present invention.

FIG. 4 illustrates a pulse detection process 60 conducted in accordance with the present invention. The pulse detection process 60 uses an analysis of impedance signal data to determine the presence of a pulse in a patient. Preferably, the impedance signal data selected for analysis is obtained during time intervals associated with QRS complexes in the patient's ECG.

Beginning at block 70 the pulse detection process 60 captures both ECG and impedance signal data, synchronized in time, for a predetermined time interval (e.g., 10 seconds). Preferably, at this time, persons around the patient are advised to not touch the patient during this time interval (e.g., the device could report "analyzing now . . . stand clear"). Alternatively, the ECG and impedance capturing step may continue until the first or a specified number of QRS complexes in the ECG have been identified, or in the event of asystole or a low heart rate, a predetermined maximum period of time (e.g., 10 seconds) has passed.

In block 72, the pulse detection process 60 locates all of the QRS complexes in the captured ECG signal. Identification of QRS complexes can be done using methods published in the literature and well-known to those skilled in the art of ECG signal processing. For example see, Watanabe K., et al., "Computer Analysis of the Exercise ECG: a Review," *Prog Cardiovasc Dis* 22: 423-446, 1980.

In block 74, for each time that a QRS complex was identified in the ECG signal, a segment of filtered impedance signal data obtained from the captured impedance data is selected. In one embodiment of the invention, the time window of each segment of impedance data is approximately 600 milliseconds in length, and commences prior to the end of the identified QRS complex. If no QRS complexes were identified in the captured ECG signal in block 72 (as would happen for example, during asystole), there will be no segments of impedance data selected in block 74.

In block 76, one or more measurements are made on a segment of impedance signal data selected in block 74 to identify or calculate a feature indicative of a cardiac pulse. The measurements may include one or more of the following:

(1) peak-to-peak amplitude of the impedance signal in the segment (measured in milliohms);

(2) peak-peak amplitude of the first derivative of the impedance signal in the segment (measured in milliohms per second);

(3) energy of the impedance signal in the segment (preferably calculated by squaring and summing each of the impedance data values in the segment); or (4) a pattern matching statistic.

As to the latter measurement (i.e., pattern matching), the segment of impedance signal data is compared with one or more previously identified impedance signal patterns known to predict the presence of a pulse. The comparison produces a pattern match statistic. Generally, in this context, the greater the value of the pattern match statistic, the closer the patient's impedance signal matches a pattern impedance signal that predicts the presence of a pulse. Other candidate measurements will be apparent to those skilled in the art, and may be used instead of, or in addition to, the aforementioned measurements. A measurement resulting from the analysis in block 76 constitutes a feature of the impedance signal data indicative of the presence of a pulse.

In decision block 78, the one or more features from block 76 are evaluated to determine the presence of a cardiac pulse in the patient. The embodiment shown in FIG. 4 compares the one or more features to predetermined thresholds to determine whether or not a pulse is detected. For example, an impedance peak-to-peak amplitude measurement would be consistent with the presence of a pulse if it exceeded a certain threshold (e.g., 50 milliohms). Similarly, an impedance energy measurement would be consistent with a pulse if its magnitude exceeded a predetermined threshold. Likewise, a pattern matching statistic would be consistent with a pulse if it exceeded a predetermined threshold. If the feature exceeded the specified threshold, the pulse detection process determines that a pulse was detected, as indicated at block 80. If the feature did not exceed the specified threshold, a pulse was not detected, as indicated at block 82. If no segments of impedance signal data were selected in block 74 (i.e., no QRS complexes were located in block 72 in the captured ECG), the pulse detection process 60 would determine that a pulse was not detected, as indicated at block 82.

The embodiment shown in FIG. 4 uses thresholding in block 78 to determine whether a pulse was detected. However, those skilled in the art will recognize other forms of classification and determination that may suitably be used in the invention. For example, multi-dimensional classifiers may be used in decision block 78 to determine whether a pulse was detected. For example, separate analyses of the amplitude and energy in the impedance data segment, may be performed, with the resultant outcome of each analysis constituting a detection statistic that is provided to a multi-dimensional classifier. The detection statistics may be weighted and compared in the classifier to determine an overall conclusion whether a pulse is present in the patient. In other embodiments, individual calculations of instantaneous and background amplitudes and/or energies may be provided as detection features for evaluation in a multi-dimensional classifier. Pattern match statistics may also be evaluated in the multi-dimensional classifier, as may other candidate measurements of the impedance signal data. Techniques for constructing multi-dimensional classifiers are well-known in the art. For an expanded description of classifiers suitable for use with of the invention, see, e.g., R. Duda and P. Hart, *Pattern Classification and Scene Analysis*, published by John Wiley & Sons, New York, and incorporated herein by reference.

After determining whether a pulse was detected (block 80) or not detected (block 82), the pulse detection process 60 determines whether all of the segments of impedance signal data selected in block 74 have been analyzed. If not, the analysis and decision process of block 76, 78, 80, and 82 is repeated for a new impedance data segment. This continues until all of the impedance data segments selected in block 74 have been analyzed, as illustrated by the decision block 84.

It is recognized that the resulting determination (pulse detected or no pulse detected) may not be the same for each impedance data segment analyzed. An additional decision step is used to determine the overall outcome of the pulse detection process 60. As indicated at decision block 86, the pulse detection process 60 may evaluate the determinations for each impedance data segment and decide that a pulse is present in the patient if a pulse was detected in a simple majority of the impedance segments analyzed. Of course, other voting schemes may be used. If, in decision block 86, a majority is found, the pulse detection process concludes that a cardiac pulse is present in the patient, as indicated at block 90. Otherwise, the pulse detection process 60 concludes that the patient is pulseless, as indicated at block 88.

Figure 5:
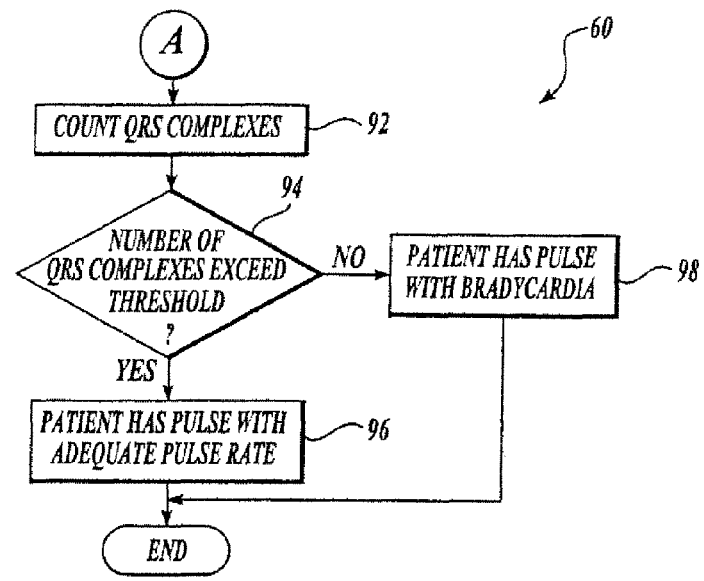
FIG. 5 is a flow diagram of a pulse rate analysis performed in accordance with the present invention the pulse detection process shown in FIG. 4.

Requiring a pulse to be found in more than a simple majority of the impedance data segments would improve the specificity of the detection, but decrease the sensitivity for detecting a pulse. Conversely, requiring a pulse to be found for just one impedance segment or for less than a majority of the impedance segments would improve sensitivity for detecting a pulse but decrease specificity. If the pulse detection process 60 concludes that a pulse is present in the patient, the process 60 may optionally proceed to check the pulse rate of the patient, as illustrated in FIG. 5. Turning to FIG. 5, in block 92, the number of QRS complexes (located in block 72 in FIG. 4) are counted. Decision block 94 subsequently compares the number of QRS complexes to a threshold. In one preferred embodiment, the threshold is 5, corresponding to a heart rate of approximately 30 bpm. If the number of QRS complexes is at least equal to the threshold, the pulse detection process 60 proceeds to block 96, concluding that the patient has a pulse and an adequate pulse rate. If the number of QRS complexes is less than the threshold, the pulse detection process 60 proceeds to block 98, concluding that the patient has a pulse, but also severe bradycardia.

Figure 6:
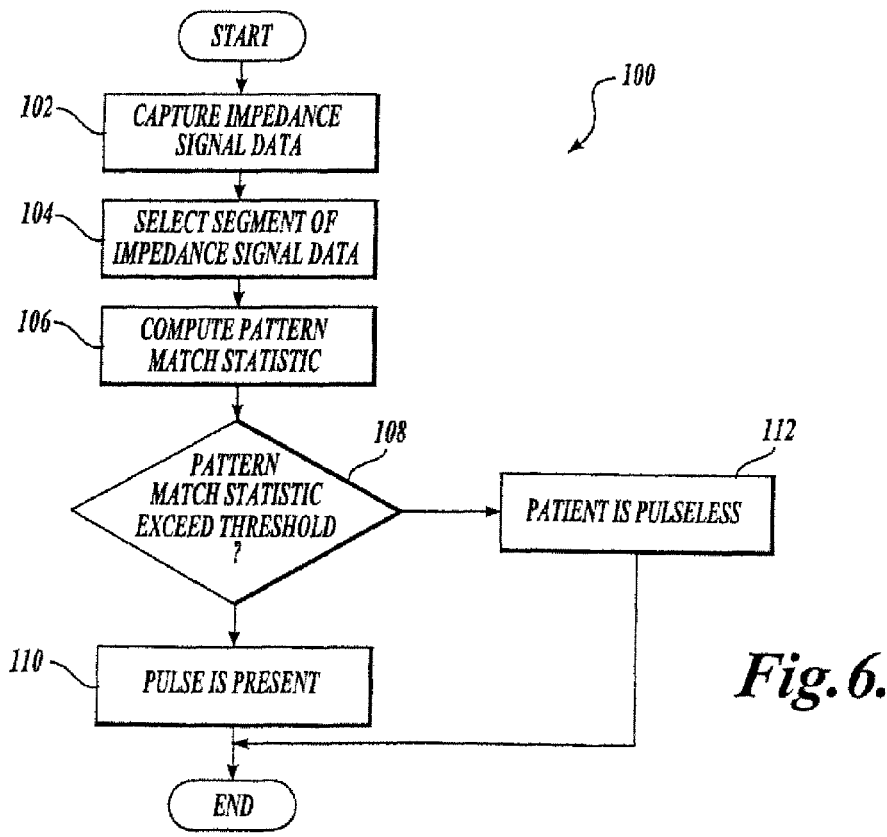
FIG. 6 is a flow diagram of another pulse detection process performed in accordance with the present invention in which an impedance signal pattern analysis is performed without an ECG signal analysis.

While a preferred embodiment of the invention as shown in FIG. 4 includes capturing both ECG and impedance signal data, and selecting the segments of impedance signal data based on QRS complexes located in the ECG, other embodiments of the invention may not capture or use the ECG signal. In FIG. 6, an alternative pulse detection process 100 begins by capturing only impedance signal data from the patient, as indicated at block 102. Depending on the length of the time interval in which impedance data is captured, it may be advantageous to select a segment of the impedance signal data for further analysis, as indicated at block 104. In that regard, one suitable selection process includes scanning the impedance signal data for the maximum peak and selecting a segment of data that surrounds the detected maximum peak.

For exemplary purposes, the pulse detection process 100 is shown evaluating the selected segment of impedance signal data using a pattern match analysis. However, those skilled in the art will recognize that other techniques (e.g., analysis of the amplitude or energy in the impedance signal data, as discussed above, may be used.) In block 106, the selected impedance data segment is compared with previously identified impedance signal patterns known to predict the presence of a pulse. The resulting pattern match statistic is evaluated against a threshold in decision block 108 to determine whether a pulse was detected in the patient. If the pattern match statistic exceeded the threshold, the pulse detection process 100 concludes in block 110 that a pulse was detected in the patient. Otherwise, the pulse detection process 100 concludes that the patient is pulseless, as indicated in block 112. At this point, the pulse detection process is finished. Alternatively, if a pulse was detected in the patient, the pulse detection process 110 may proceed to evaluate the patient's pulse rate in a manner described in reference to FIG. 5.

As noted above, the transthoracic impedance signal can contain fluctuations due to cardiac pulses, respiration, or patient motion. To assess whether a patient has a pulse, it is desirable to suppress fluctuations in the patient's impedance that are due to causes other than cardiac pulses. Fluctuations due to noncardiac causes may contain components at frequencies similar to those of impedance fluctuations due to cardiac pulses. Consequently, bandpass filtering may not always adequately suppress fluctuations due to noncardiac causes.

Signal averaging of the impedance signal can be used to suppress fluctuations that are due to noncardiac causes. Signal averaging makes advantageous use of the fact that impedance fluctuations due to cardiac pulses are synchronized to QRS complexes in the ECG signal, whereas other impedance fluctuations are asynchronous to QRS complexes. Pulse detection may be more accurately accomplished using an averaged impedance signal.

A preferred method for signal averaging of the impedance signal first stores the continuous ECG and transthoracic impedance signals, synchronized in time, for a predetermined time interval (e.g., ten seconds). The locations of the QRS complexes (if any) in the stored ECG signal are determined. Using true mathematical correlation (or an alternative correlation technique such as area of difference), the QRS complexes are classified into types, where all QRS complexes of the same type have high correlation with the first occurring QRS complex of that type. The dominant QRS type is selected as the type containing the most members, with a preference for the narrowest QRS type when a two or more types tie for most members. Using the first QRS of the dominant type as a reference complex, the second QRS complex of the same type is shifted in time until it is best aligned with the reference complex (i.e., it achieves a maximum correlation value). The corresponding impedance signal is also shifted in time to stay synchronized with the time-shifted QRS complex. When the second QRS complex is optimally aligned with the reference complex, the two QRS complexes are averaged together. Their corresponding impedance signals, over a time period from about the start of the QRS complex to about 600 milliseconds after the end of the QRS complex, are also averaged together. The averaged QRS complex is then used as a new reference complex and the process of averaging both the QRS complexes and the corresponding impedance data is repeated with the remaining QRS complexes of the dominant type.

Preferably, during the subsequent averaging of the QRS complexes and impedance segments, the new QRS complex and impedance segment carry a weight of one and the previous averaged QRS complex and impedance segment carry a weight equal to the number of QRS complexes that have been included in the averaged QRS complex. When all of the QRS complexes of the dominant type have been processed as described above, the averaged impedance segment is evaluated using one or more of the techniques previously described (e.g., amplitude, energy, pattern matching), or by using another measuring technique known in the art, to determine whether or not the patient has a pulse.

During severe bradycardia, there will be few QRS complexes in a 10-second period and signal averaging of the transthoracic impedance signal will not be as effective as when the heart rate is higher. However, at very low heart rates, there is unlikely to be enough blood flow to support life. For that reason, below a certain heart rate (e.g., 30 bpm), the patient may be considered pulseless.

Figure 7:
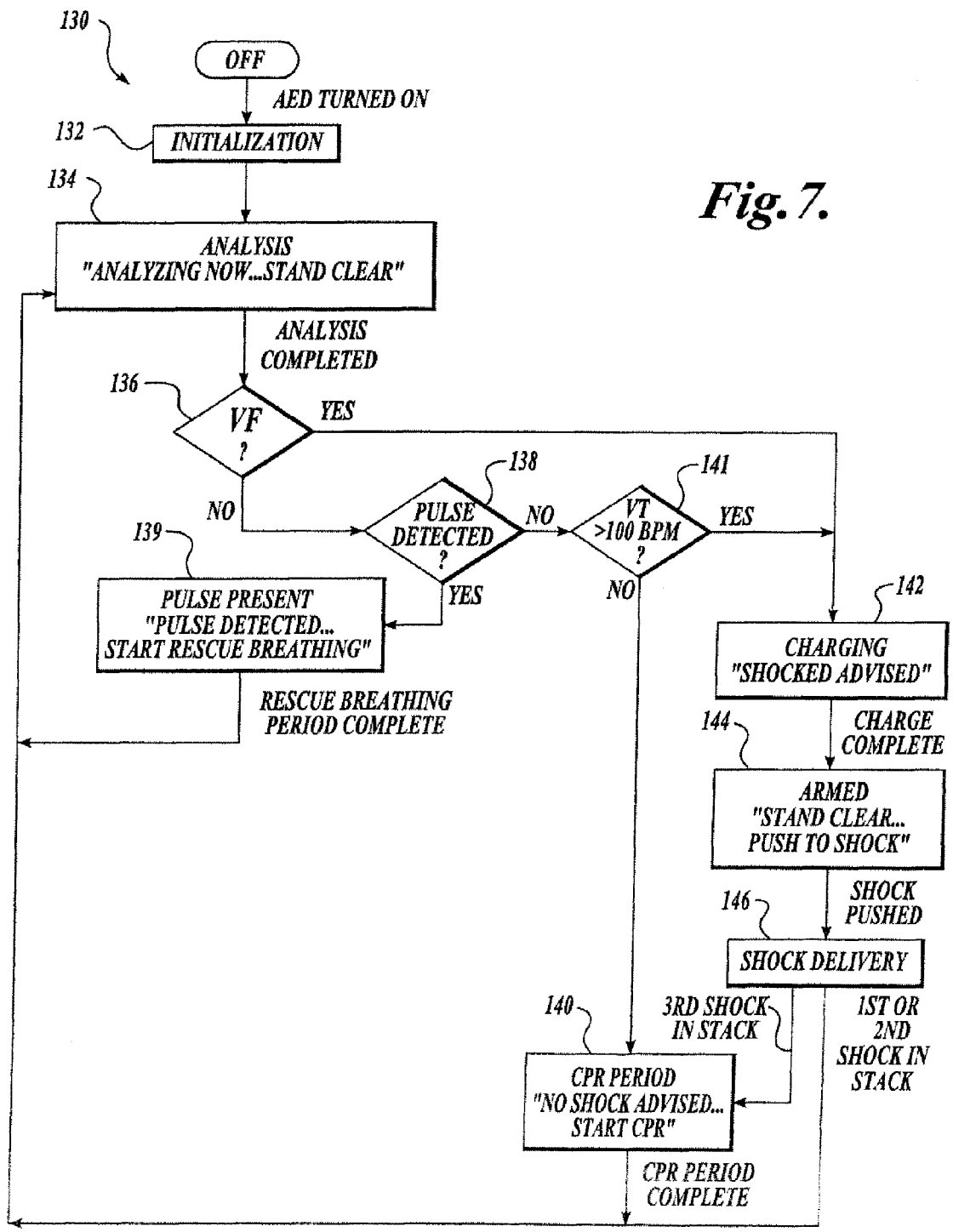
FIG. 7 is a flow diagram of a protocol implemented by a defibrillator as shown in FIG. 2 that incorporates a pulse detection process provided by the present invention.

The pulse detection process of the present invention may be used as part of a shock advisory protocol in a defibrillator for determining whether to recommend defibrillation or other forms of therapy for the patient. FIG. 7 illustrates a pulse detection/defibrillation process 130, preferably for use in an automated external defibrillator (AED) capable of providing a defibrillation pulse if a patient is determined to be pulseless and in VF or VT.

In the pulse detection/defibrillation process 200 in FIG. 7, the AED initializes its circuits when it is first turned on, as indicated at block 132. The defibrillation electrodes of the AED are placed on the patient. When the AED is ready for operation, the process 130 performs an analysis of the patient, as indicated at block 134, in which the AED obtains selected parameters such as impedance signal data and ECG data from the patient. During the analysis performed in block 134, the AED preferably reports "Analyzing now . . . stand clear" to the operator of the AED.

Using the information obtained in the patient analysis, the process 130 determines in decision block 136 whether the patient is experiencing ventricular fibrillation (VF). If VP is present in the patient, the process 130 proceeds to block 142 where the AED prepares to deliver a defibrillation pulse to the patient. In that regard, an energy storage device within the AED, such as a capacitor, is charged. At the same time, the AED reports "Shock advised" to the operator of the AED.

Once the energy storage device is charged, the process 130 proceeds to block 144 where the AED is ready to deliver the defibrillation pulse. The operator of the AED is advised "Stand clear . . . push to shock." When the operator of the AED initiates delivery of the defibrillation pulse, the process 130 delivers the defibrillation shock to the patient, as indicated in block 146.

The AED preferably records in memory that it delivered a defibrillation pulse to the patient. If the present pulse delivery is the first or second defibrillation shock delivered to the patient, the process 130 may return to block 134 where the patient undergoes another analysis. On the other hand, if the pulse delivery was the third defibrillation pulse to be delivered to the patient, the process 130 may proceed to block 140 where the AED advises the operator to commence providing CPR therapy to the patient, e.g., by using the message "Start CPR." The "No shock advised" prompt shown in block 140 is suppressed in this instance. The AED may continue to prompt for CPR for a predetermined time period, after which the patient may again be analyzed, as indicated in block 134.

Returning to decision block 136, if VF is not detected in the patient, the process 130 proceeds to decision block 138 and determines whether a cardiac pulse is present in the patient. The pulse detection performed in block 138 may be one of the pulse detection processes 60 or 100 described above.

If, at decision block 138, a pulse is detected in the patient, the process 130 proceeds to block 139 and reports "Pulse detected . . . start rescue breathing" to the operator. The process 130 may also report "Return of spontaneous circulation" if a pulse is detected in the patient any time after the delivery of a defibrillation pulse in block 146. In any event, after a predetermined time period for rescue breathing has completed, the process 130 preferably returns to block 134 to repeat an analysis of the patient.

If a cardiac pulse is not detected at decision block 138, the process 130 determines whether the patient is experiencing ventricular tachycardia (VT) with a heart rate of greater than a certain threshold, e.g., 100 beats per minute (bpm), as indicated at decision block 141. Other thresholds such as 120, 150, or 180 bpm, for example, may be used. If the determination at decision block 141 is negative, the process 130 proceeds to block 140 and advises the operator to provide CPR therapy. Again, at this point, the AED reports "No shock advised . . . start CPR" to the operator. The prompt to provide CPR is provided for a defined period of time. When the period of time for CPR is finished, the process 130 preferably returns to block 134 and performs another analysis of the patient. If the determination at decision block 141 is positive (i.e., the patient is experiencing VT with a heart rate greater than the threshold), the process 130 performs the shock sequence shown at blocks 142, 144, 146 to deliver a defibrillation pulse.

Figure 8:
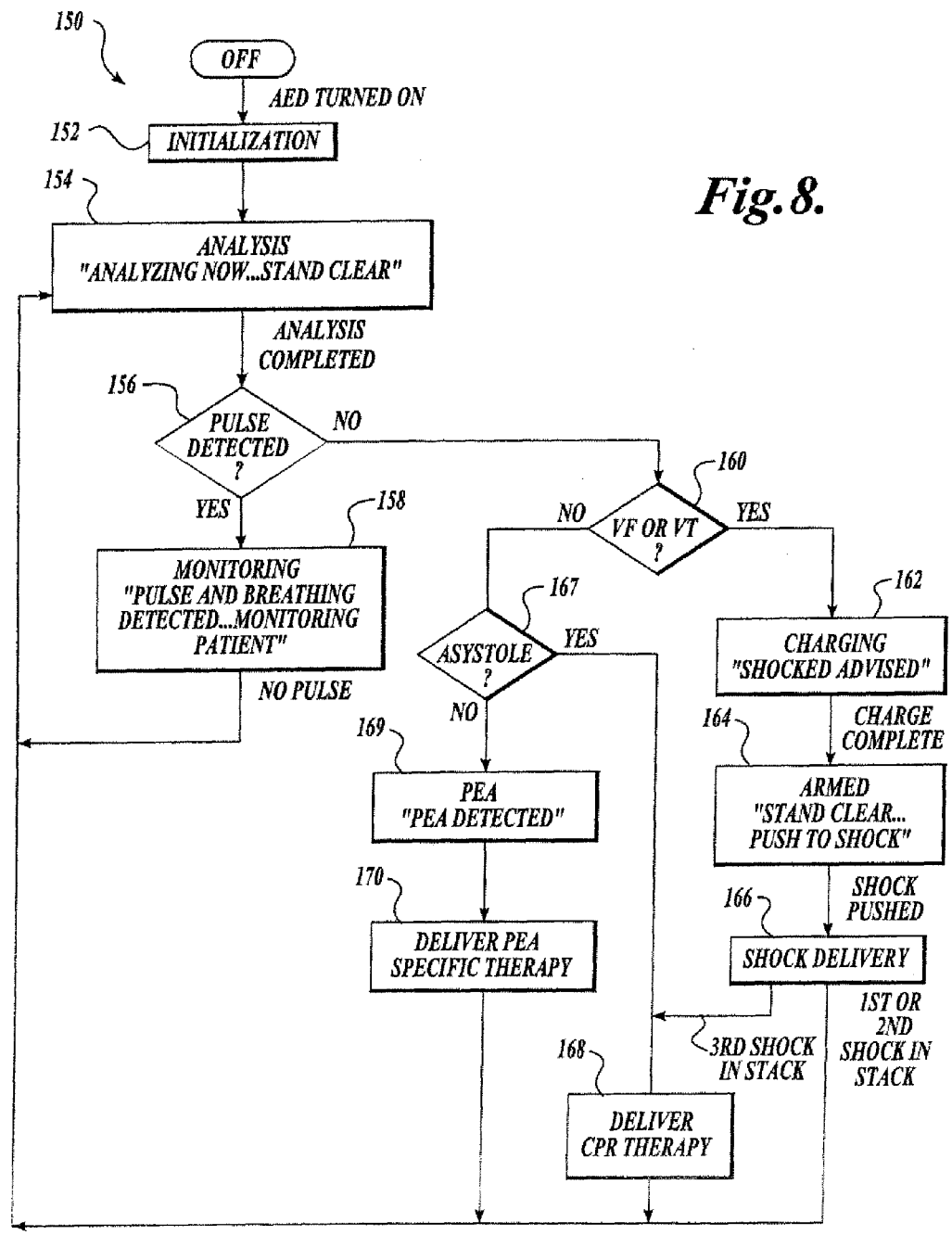
FIG. 8 is a flow diagram of protocol implemented by the defibrillator shown in FIG. 2 that incorporates a pulse detection process provided by the present invention.

Variations and additions to the process 130 within the scope of the invention are recognized by those having ordinary skill in defibrillation and cardiac therapy. FIG. 8, for example, illustrates an alternative pulse detection/defibrillation process 150 for use in an AED. As with the process 130 in FIG. 7, the AED begins by initializing its circuits at block 152. At block 154, the AED performs an analysis of the patient in a manner similar to that described with respect to block 134 in FIG. 7. After completing the analysis of the patient, the process 150 proceeds to decision block 156 to determine whether a pulse is present in the patient. The pulse detection performed in block 156 may be, for example, any one of the pulse detection processes 60 or 100 discussed above.

If a pulse is detected in the patient, the process 150 may enter a monitoring mode at block 158 in which the patient's pulse is monitored. The pulse monitoring performed at block 158 may use any one or a combination of the pulse detection processes described herein. Preferably, the process 150 is configured to proceed from block 158 to block 154 after expiration of the predetermined monitoring time period. If the pulse monitoring at block 158 determines that at any time a pulse is no longer detected, the process 150 returns to block 154 to perform another analysis of the patient. The process 150 also preferably reports the change in patient condition to the operator.

If, at decision block 156, a pulse is not detected in the patient, the process 150 proceeds to decision block 160 where it determines whether the patient has a shockable cardiac rhythm (e.g., VF or VT). As referenced earlier, U.S. Pat. No. 4,610,254, incorporated herein by reference, describes a suitable method for differentiating shockable from non-shockable cardiac rhythms.

If a shockable cardiac rhythm, such as VF or VT, is detected, the process 150 proceeds to a shock delivery sequence at blocks 162, 164, and 166, which may operate in a manner similar to that described with respect to blocks 142, 144, and 146 in FIG. 7. If the pulse delivery was the third defibrillation shock delivered to the patient, the process 150 may proceed to block 168 and prompt the delivery of CPR, as discussed with block 140 in FIG. 7.

If VF or VT is not detected at decision block 160, the process 150 checks for asystole, as indicated at block 167. One suitable process for detecting asystole is described in U.S. Pat. No. 6,304,773, assigned to the assignee of the present invention and incorporated herein by reference. If asystole is detected at block 167, the process 150 proceeds to prompt the delivery of CPR, as indicated at block 168. If asystole is not detected, the process 150 determines that the patient is experiencing pulseless electrical activity (PEA), as indicated at block 169. PEA is generally defined by the presence of QRS complexes in a patient and the lack of a detectable pulse, combined with no detection of VT or VF. As described above, detection of PEA in block 168 is achieved by ruling out the presence of a pulse (block 156), detecting no VF or VT (block 160), and detecting no asystole (block 167). Alternatively, if the ECG signal is monitored for QRS complexes (e.g., as shown at block 70 in FIG. 4), the process 150 may conclude the patient is in a state of PEA if it repeatedly observes QRS complexes without detection of a cardiac pulse associated therewith. If a PEA condition is detected, the process 150 proceeds to block 170 and prompts the operator to deliver PEA-specific therapy to the patient. One suitable method of treating PEA is described in U.S. Pat. No. 6,298,267, incorporated by reference herein. The process 150 may prompt other therapies as well, provided they are designed for a PEA condition. After a PEA-specific therapy has been delivered to the patient, possibly for a predetermined period of time, the process 150 returns to block 154 to repeat the analysis of the patient.

Figure 9:
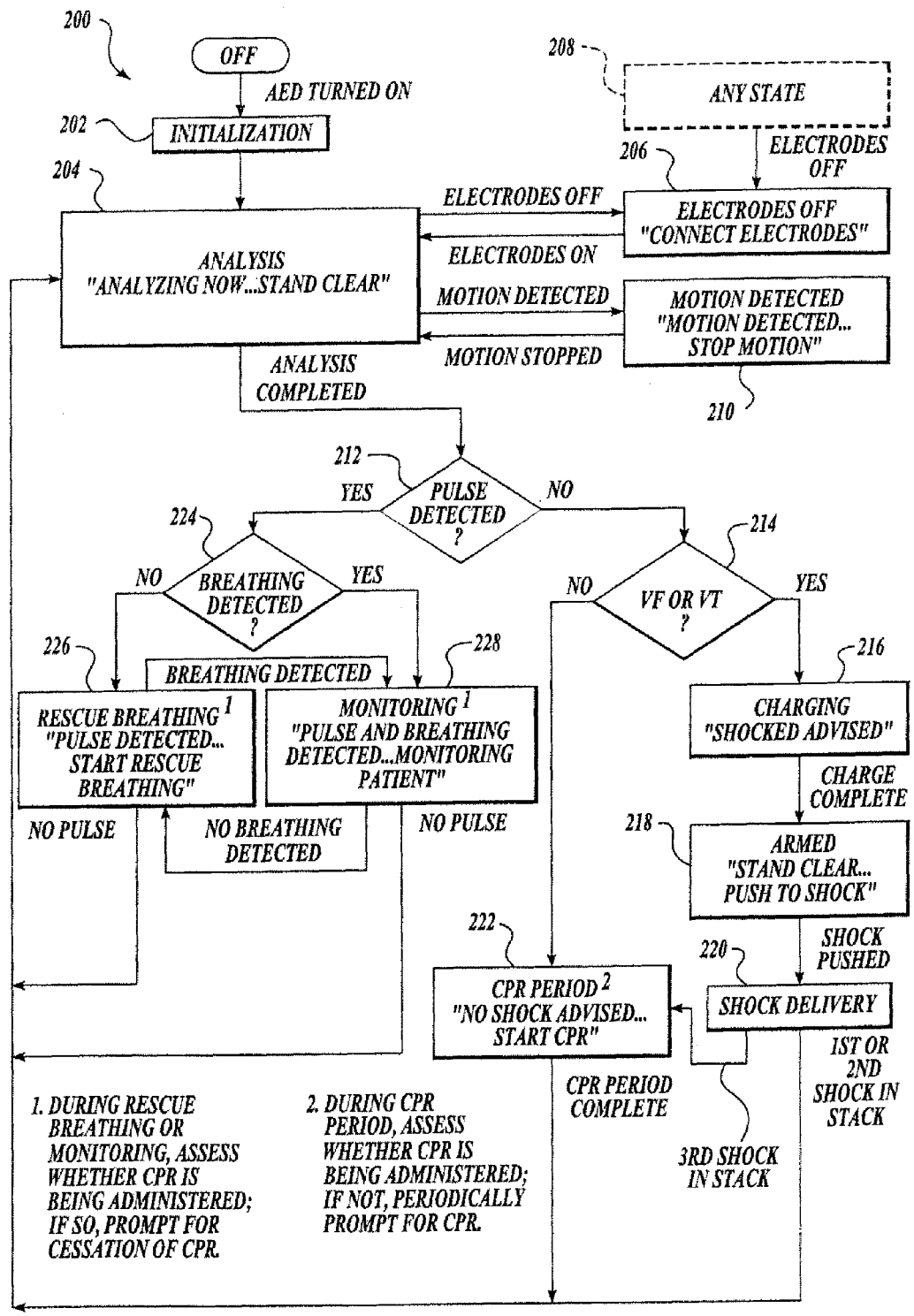
FIG. 9 is a flow diagram of still another protocol implemented by the defibrillator shown in FIG. 2 that incorporates a pulse detection process provided by the present invention.

FIG. 9 illustrates yet another pulse detection/defibrillation process 200 that may be used in an AED. At block 202, after the AED has been turned on, the AED initializes its circuits. The defibrillation electrodes are also placed on the patient. The AED is then ready to analyze the patient, as indicated at block 204. This analysis may be performed in a manner similar to that described with respect to block 134 in FIG. 7.

If at any point the AED determines that the defibrillation electrodes are not connected to the AED, the process 200 jumps to block 206 where the AED instructs the operator to "Connect electrodes." When the AED senses that the electrodes are connected, the process 200 returns to the analysis in block 204. Likewise, if the AED finds itself in any other state where the electrodes are not connected, as represented by block 208, the process 200 jumps to block 206 where it instructs the operator to connect the electrodes.

Furthermore, during the analysis performed in block 204, if the AED detects motion on the part of the patient, the process 200 proceeds to block 210 where the AED reports to the operator of the AED "Motion detected . . . stop motion." If the patient is moved during the analysis process 204, the data obtained during the analysis is more likely to be affected by noise and other signal contaminants. Motion of the patient may be detected in the impedance signal data collected by the present invention. A suitable method for detecting motion of the patient is described in U.S. Pat. No. 4,610,254, referenced earlier and incorporated by reference herein. The AED evaluates the impedance measured between the defibrillation electrodes placed on the patient. As noted earlier, noise and signal components resulting from patient motion cause fluctuations in the impedance signal, generally in a frequency range of 1-3 Hz. If the measured impedance fluctuates outside of a predetermined range, the AED determines that the patient is moving or being moved and directs the process 200 to proceed to block 210. When the motion ceases, the process 200 returns to the analysis in block 204.

The process 200 next proceeds to decision block 212 where it determines whether a pulse is detected in the patient. Again, the pulse detection processes performed in decision block 212 may be, for example, one of the pulse detection processes 60 or 100 described above.

If a pulse is not detected in the patient, the process 200 proceeds to decision block 214 where it determines whether the patient has a shockable cardiac rhythm (e.g., VF or VT or a non-shockable cardiac rhythm (such as asystole and bradycardia). As referenced earlier, one suitable method for differentiating shockable from non-shockable cardiac rhythms is disclosed in U.S. Pat. No. 4,610,254, incorporated herein by reference. If the patient's cardiac rhythm is determined to be shockable (e.g., VF or VT is found), the process 200 proceeds to blocks 216, 218, and 220 to deliver a shock to the patient. The shock delivery may be performed as described earlier with respect to block 142, 144, 146 in FIG. 7.

If the pulse delivery was the third defibrillation pulse to be delivered to the patient, the process 200 proceeds to block 222 where the AED advises the operator to commence providing CPR therapy to the patient. The CPR prompt may continue for a defined period of time, at which the process 200 returns to block 204 and performs another analysis of the patient.

If, at decision block 214, the patient's cardiac rhythm is determined not shockable, the process 200 preferably proceeds to block 222 and advises the operator to provide CPR therapy, as discussed above.

Returning to decision block 212, if a pulse is detected in the patient, the process 200 proceeds to decision block 224 where it determines whether the patient is breathing. In that regard, the AED may again use the impedance signal for determining whether a patient is breathing. As noted earlier, fluctuations in impedance of the patient below 1 Hz are largely indicative of a change in volume of the patient's lungs. The breathing detection at block 224 (and at blocks 226 and 228, discussed below) may monitor the impedance signal for characteristic changes that indicate patient breathing, e.g., as described in Hoffmans et al., "Respiratory Monitoring With a New Impedance Plethysmograph," *Anesthesia* 41: 1139-42, 1986, and incorporated by reference herein. Detection of breathing may employ a process similar to that described above for detection of a pulse (i.e., evaluating impedance amplitude, energy, or pattern), though a different bandpass filter would be used to isolate the frequency components that more closely demonstrate patient breathing. If automatic means for detecting breathing in the patient are not available, the AED may ask the operator of the AED to input information (e.g., by pressing a button) to indicate whether the patient is breathing.

If, at decision block 224, the process 200 determines that the patient is not breathing, the process 200 proceeds to a block 226 where the operator of the AED is advised to commence rescue breathing. In that regard, the AED reports to the operator "Pulse detected . . . start rescue breathing." The AED also continues to monitor the patient's cardiac pulse and returns to block 204 if a cardiac pulse is no longer detected. If, at any point during the provision of rescue breathing, the AED detects that the patient is breathing on his own, the process 200 proceeds to block 228 where the AED monitors the patient for a continued presence of breathing and a cardiac pulse.

Returning to decision block 224, if the process 200 determines that the patient is breathing, the process 200 proceeds to block 228 where the AED monitors the pulse and breathing of the patient. In that regard, the AED reports "Pulse and breathing detected . . . monitoring patient." If, at any time during the monitoring of the patient the process 200 determines that the patient is not breathing, the process 200 proceeds to block 226 where the operator of the AED is advised to commence rescue breathing. If a cardiac pulse is no longer detected in the patient, the process 200 proceeds from block 228 to block 204 to commence a new analysis of the patient.

Lastly, as noted in FIG. 9, during the rescue breathing procedure in block 226 or the monitoring procedure performed in block 228, the AED may assess whether CPR is being administered to the patient. If the AED finds that CPR is being performed, the AED may prompt the operator to cease providing CPR. If, during the CPR period of block 222, the AED determines that CPR is not being administered to the patient, the AED may remind the operator to provide CPR therapy to the patient. One method for determining whether CPR is being administered is to monitor patient impedance to observe patterns of impedance fluctuation in the patient that are indicative of CPR. During CPR, repetitive chest compression typically causes repetitive fluctuations in the impedance signal.

Figure 10:
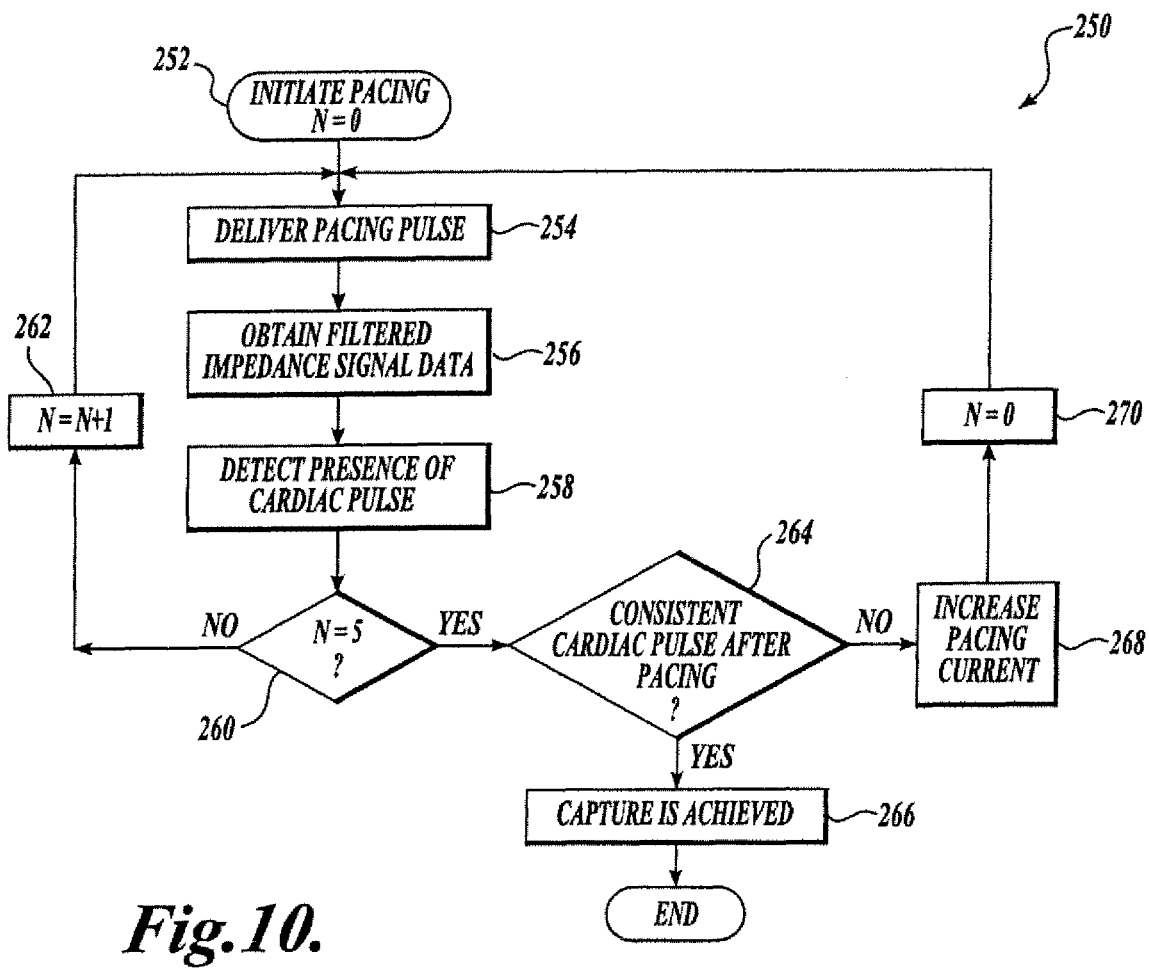
FIG. 10 is a flow diagram of an auto-capture detection process for cardiac pacing that uses a pulse detection process of the present invention.

FIG. 10 illustrates yet another application in which the pulse detection process of the present invention may be used. The process described in FIG. 10 pertains to auto-capture detection in cardiac pacing.

Specifically, the auto-capture detection process 250 begins at block 252 in which pacing therapy for the patient is initiated. A counter N, described below, is set to equal 0. At block 254, a pacing pulse is delivered to the patient. Thereafter, filtered impedance signal data is obtained from the patient, as indicated at block 256. The impedance data is used in block 258 to detect the presence of a cardiac pulse in the patient. The pulse detection process used in block 258 may be one of the pulse detection processes 60 or 100, discussed above.

The sequence of delivering a pacing pulse and determining the presence of a cardiac pulse in blocks 254, 256, 258 is repeated a predetermined number of times. With respect to FIG. 10, for example, the sequence is repeated five times. At block 260, the counter N is evaluated, and if not yet equal to 5, the counter is incremented by 1 (block 262), following which the process 250 returns to deliver another pacing pulse to the patient.

If, at decision block 260, the counter N equals 5, the process 250 determines at decision block 264 whether a cardiac pulse occurred consistently after each pacing pulse. The process 250 requires that some portion or all of the pacing pulses result in a detectable cardiac pulse before pronouncing that capture has been achieved. If the presence of a cardiac pulse is determined consistently follow the pacing pulses, the process 250 determines that capture has been achieved, as in indicated at block 266. Otherwise, the current of the pacing pulses is increased by a predetermined amount, e.g., 10 milliamperes, as indicated at block 268. At block 270, the counter N is set back to equal 0 and the process 250 returns to the pacing capture detection sequence beginning at block 254. In this manner, the pacing current is increased until capture has been achieved.

In FIG. 10, the presence of a pulse is used to determine whether the pacing stimulus has been captured by the ventricles. Detection of QRS complexes in the patient's ECG may also be used to identify pacing capture. In that regard, the patient's ECG would be monitored along with, or in place of, the impedance data collection in block 256. A QRS complex will occur immediately following the pacing stimulus if capture has been achieved. If QRS complexes are not observed, the current of the pacing pulses may be increased, as discussed above, until capture has been achieved.

Figure 11:
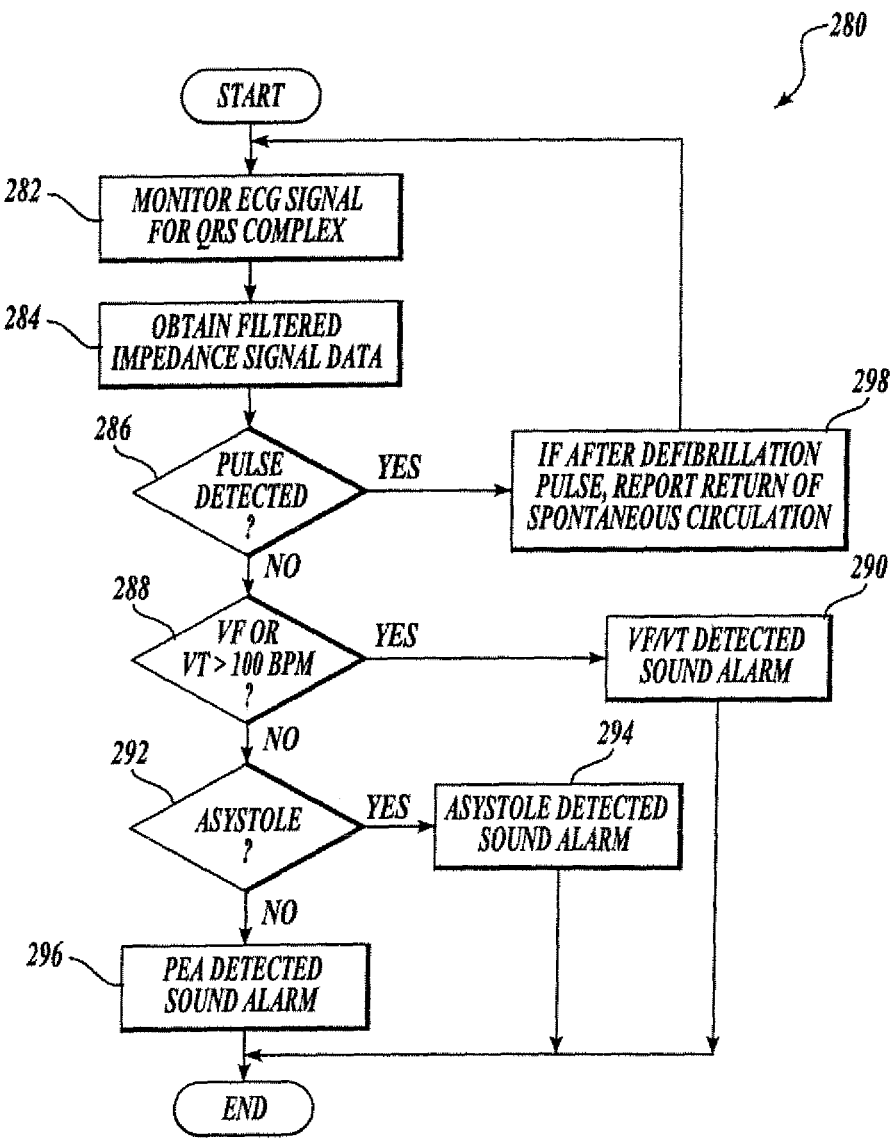
FIG. 11 is a flow diagram of a patient condition advisory process for use in a manual defibrillator or monitor which incorporates a pulse detection process of the present invention.

FIG. 11 illustrates still another application in which the pulse detection process of the present invention may be used. The process 280 described in FIG. 11 is particularly suited for use in a manual defibrillator or patient monitor. Beginning at block 282, the process 280 monitors the patient's ECG for QRS complexes. At block 284, the process 280 also obtains filtered impedance signal data from the patient. The process 280 uses the ECG and impedance signals in decision block 286 to determine the presence of a pulse. The pulse detection implemented in block 286 may be one of the pulse detection processes 60 or 100.

If a pulse is detected, the process 280 determines whether a defibrillation pulse has been provided to the patient and if so, reports the return of spontaneous circulation to the operator, as indicated at block 298. The process 280 then returns to block 282 to repeat the pulse detection analysis. If a pulse is not detected, the process 280 evaluates the ECG signal to determine whether the patient is experiencing ventricular fibrillation or ventricular tachycardia with a heart rate great than 100 bpm at decision block 288. If so, then the process identifies the patient's condition and sounds a VT/VF alarm, as indicated at block 290. If not, the process 280 then proceeds to block 292 to check for an asystole condition.

Detection of asystole may be accomplished as noted earlier and described in greater detail in U.S. Pat. No. 6,304,773, incorporated herein by reference. If asystole is detected, the process 280 identifies the patient's condition and sounds an asystole alarm, as indicated at block 294. Otherwise, the patient is experiencing PEA and the patient's condition is so identified, with the sound of a PEA alarm, as indicated at block 296. In this manner, the operator of the manual defibrillator or monitor is kept advised of the patient's condition.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of determining the presence of a cardiac pulse in a patient, comprising:
   (a) obtaining data derived from an impedance-sensing signal that has been communicated from the patient;
   (b) analyzing the obtained impedance signal data for a feature indicative of the presence of a cardiac pulse, wherein analyzing the impedance signal data includes comparing the impedance signal data to a previously-identified impedance signal data pattern known to predict the presence of a cardiac pulse; and
   (c) determining whether a cardiac pulse is present in the patient based on the feature in the impedance signal data.

2. The method of claim 1, wherein the comparison produces a pattern match statistic that is the feature indicative of the presence of a cardiac pulse, the method further comprising comparing the feature to a predetermined pattern match threshold to determine whether a cardiac pulse occurred in the patient.

3. The method of claim 1, further comprising analyzing the impedance signal data for two or more features indicative of the presence of a cardiac pulse, wherein one of the features is determined from the comparison of the impedance signal data with a previously identified impedance signal data pattern and wherein one of the other features is determined from an evaluation of an amplitude of the impedance signal data or energy in the impedance signal data.

4. The method of claim 1, further comprising prompting delivery of chest compressions or cardiopulmonary resuscitation to the patient if a cardiac pulse is determined not present in the patient.

5. The method of claim 1, further comprising:
   (a) obtaining electrocardiogram (ECG) data from the patient; and
   (b) determining the presence of a QRS complex in the ECG data, wherein analyzing the obtained impedance signal data for a feature indicative of the presence of a cardiac pulse further includes determining whether a QRS complex occurred in the ECG data.

6. The method of claim 5, further comprising locating a QRS complex in the ECG data and selecting impedance signal data for the pattern match comparison based on the located QRS complex.

7. The method of claim 1, wherein analyzing the obtained impedance signal data further includes determining cardiac output in terms of a stroke volume or rate of output, wherein the determined cardiac output is used as an additional feature indicative of the presence of a cardiac pulse, and wherein the cardiac output feature is compared to a predetermined output threshold to determine whether a cardiac pulse is present in the patient.

8. A medical device, comprising:
- (a) electrodes adapted for placement on a patient to sense an impedance-sensing signal that has been communicated from the patient;
- (b) a conversion circuit in communication with the electrodes for converting the sensed impedance-sensing signal into digital impedance signal data; and
- (c) a processing unit in communication with the conversion circuit for processing the impedance signal data, wherein the processing unit is configured to
  - (i) analyze the impedance signal data for a feature indicative of the presence of a cardiac pulse by comparing the impedance signal date to a previously-identified impedance signal data pattern known to predict the presence of a cardiac pulse, and
  - (ii) determine whether a cardiac pulse is present in the patient based on the feature in the impedance signal data.

9. The medical device of claim 8, wherein the comparison produces a pattern match statistic that is the feature indicative of the presence of a cardiac pulse, the processing unit being further configured to compare the feature to a predetermined pattern match threshold to determine whether a cardiac pulse is present in the patent.

10. The medical device of claim 8, wherein the conversion circuit and the processing unit are implemented in a defibrillator.

11. The medical device of claim 10, wherein the defibrillator is an automated external defibrillator.

12. The medical device of claim 8, wherein the processing unit is further configured to analyze the impedance signal data by determining a cardiac output in terms of a stroke volume or rate of output and use the determined cardiac output as an additional feature indicative of the presence of a cardiac pulse, the processing unit being further configured to compare the additional feature to a predetermined cardiac output threshold to determine whether a cardiac pulse is present in the patient.

13. The medical device of claim 8, further comprising a display in communication with the processing unit wherein the processing unit is further configured to prompt a message on the display reporting whether a cardiac pulse is present in the patient.

14. The medical device of claim 8, further comprising a display in communication with the processing unit, wherein the processing unit is further configured to provide a graph on the display showing a representation of the impedance signal data.

15. The medical device of claim 8, further comprising electrodes adapted to sense electrocardiogram (ECG) signals in the patient, wherein the conversion circuit further converts the ECG signal received from the patient into digital ECG data, and wherein the processing unit is further configured to analyze the ECG data, determine the presence of a QRS complex in the ECG data, and select impedance signal data corresponding in time with the QRS complex for the analysis of the impedance signal data.

16. The medical device of claim 8, wherein the processing unit is configured to analyze the impedance signal data for two or more features indicative of the presence of cardiac pulse, wherein one of the features is determined from the comparison of the impedance signal data with a previously-identified impedance signal data pattern and wherein one of the other features is determined from an evaluation of an amplitude of the impedance signal data or an energy impedance signal data.

* * * * *